United States Patent [19]

Percival et al.

[11] 4,163,846
[45] Aug. 7, 1979

[54] SUBSTITUTED PYRAZOLOPYRIMIDINE COMPOUNDS

[75] Inventors: Albert Percival; Philip N. Judson, both of Cambridge, England

[73] Assignee: Fisons Limited, London, England

[21] Appl. No.: 796,827

[22] Filed: May 13, 1977

[30] Foreign Application Priority Data

May 15, 1976 [GB] United Kingdom ............... 20147/76

[51] Int. Cl.$^2$ ....................... C07D 487/04; A01N 9/22
[52] U.S. Cl. ......................................... 544/262; 71/92; 542/422; 544/118
[58] Field of Search ........................ 544/262; 542/450; 71/92

[56] References Cited

U.S. PATENT DOCUMENTS

| 3,098,075 | 7/1963 | Druey et al. ........................ 544/262 |
| 3,211,728 | 10/1965 | Druey et al. ........................ 544/262 |

Primary Examiner—Donald G. Daus
Assistant Examiner—James H. Turnipseed
Attorney, Agent, or Firm—Wenderoth, Lind & Ponack

[57] ABSTRACT

There are provided, as novel herbicides, the substituted pyrazolopyrimidines of the formula:

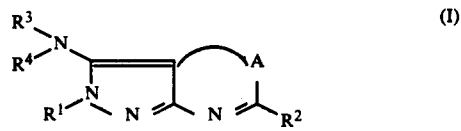

where A represents -CO-NR$^6$- or -C(OR$^7$)=N-, and R$^1$, R$^2$, R$^3$, R$^4$, R$^6$ and R$^7$ are substituent groups as defined in the specification, and the salts and acid addition salts thereof. Processes for their preparation are provided, as also are herbicidal compositions containing them and methods of combating weeds in which they are used.

10 Claims, No Drawings

SUBSTITUTED PYRAZOLOPYRIMIDINE COMPOUNDS

This invention concerns new compounds, processes for their preparation, and herbicidal compositions containing them.

The new compounds of the invention are the substituted pyrazolopyrimidines or the formula:

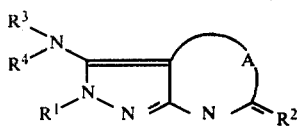

(wherein $R^1$ represents hydrogen or a substituted or unsubstituted alkyl, cyclalkyl, phenyl or heterocyclyl group; $R^2$ represents hydrogen, hydroxy, alkyl, halo, haloalkyl, hydroxy-alkyl, alkenyl, alkynyl, cycloalkyl, aryl, aralkyl, heterocyclyl or a group $-S(O)_nR^5$ where $n=0$, 1 or 2 and $R^5$ represents an alkyl, aryl or aralkyl group or, when $n=0$, a hydrogen atom; $R^3$ and $R^4$, which may be the same or different, each represent hydrogen, an alkyl, aryl, aralkyl, acyl, alkanesulphonyl, alkoxycarbonyl, carbamoyl or alkylated carbamoyl group, or $R^3$ and $R^4$, together with the nitrogen atom to which they are attached, form a heterocyclic ring system, or $R^3$ and $R^4$ together represent a group $=CR^8R^9$, where $R^8$ and $R^9$, which may be the same or different, each represent hydrogen or substituted or unsubstituted alkyl, phenyl or heterocyclyl, or, together with the carbon atom to which they are attached, represent cycloalkyl; and A represents a group $-CO-NR^6-$ or a group $-C(OR^7)=N-$, the carbon atom of which is attached to the pyrazole ring, wherein $R^6$ represents hydrogen, a substituted or unsubstituted alkyl, alkenyl, alkynyl, or cycloalkyl group, an amino group, an alkylamino group or a dialkylamino group, and $R^7$ represents hydrogen or a substituted or unsubstituted alkyl group); and salts and acid addition salts thereof.

When $R^1$ represents an unsubstituted alkyl group, as is preferred, it-is preferably a C 1 to 6, especially a C 1 to 4, alkyl group, for example methyl, ethyl, n-propyl, iso-propyl, or n-butyl.

When $R^1$ represents a substituted alkyl group, it is preferably a substituted C 1 to 6 alkyl group, for example a substituted C 1 to 4 alkyl group, for example a substituted methyl, ethyl or n-propyl group. The preferred substituent groups are halogen atoms, for example fluorine, chlorine or bromine, hydroxy groups, hydroxysulphonyloxy groups and cyano groups, and specific preferred substituted alkyl groups which $R^1$ may represent are 2-chloroethyl, 2-bromoethyl, 2-hydroxyethyl, 2-hydroxypropyl, cyanomethyl or 2-hydroxysulphonyloxyethyl.

When $R^1$ represents a cycloalkyl group, it is preferably an unsubstituted cycloalkyl group, and is preferably of 3 to 7 carbon atoms, e.g. cyclopentyl or cyclohexyl.

When $R^1$ represents a phenyl group, it is preferably an unsubstituted phenyl group. When, however, it represents a substituted phenyl group, the substituent(s) thereon are preferably nitro, halogen, especially chlorine, C 1 to 4 alkyl, especially methyl, or C 1 to 4 alkoxy, especially methoxy. Specific preferred substituted phenyl groups are monosubstituted, e.g. 4-methylphenyl-2-methoxyphenyl, 3-nitrophenyl and 4-chlorophenyl. Disubstituted phenyl groups which may be mentioned include 3,4-dichlorophenyl and 2,4-dimethylphenyl.

When $R^1$ represents a heterocyclyl group, it is preferably an oxygen, nitrogen or sulphur-containing heterocycle, especially a 5- or 6-membered heterocycle, either saturated or unsaturated, for example piperidino, pyridyl, pyrrolyl, morpholino, furyl or thienyl.

When R1 represents a substituted heterocyclyl group, the or each substituent is preferably halogen especially chlorine, or C 1 to 4 alkyl, especially methyl. Specific preferred groups are 5-chloro-2-pyridyl and 4-methyl-2-furyl.

When $R^2$ represents an alkyl, haloalkyl or hydroxyalkyl group, as is preferred, it is preferably such a group having from 1 to 6 carbon atoms and especially from 1 to 4 carbon atoms. Specific preferred alkyl groups which $R^2$ may represent are methyl, ethyl, isopropyl and t-butyl, preferred haloalkyl groups are trifluoromethyl and chloromethyl, and a preferred hydroxyalkyl group is 2-hydroxyethyl.

When $R^2$ represents halo, it is preferably chloro or bromo.

When $R^2$ represents an alkenyl or alkynyl group, it is preferably such a group having from 2 to 6 carbon atoms, for example vinyl, allyl or propargyl.

When $R^2$ represents a cycloalkyl group, it is preferably such a group having from 3 to 7, especially 5 or 6, carbon atoms, e.g. cyclopentyl or cyclohexyl.

When $R^2$ represents an aryl group, it is preferably a phenyl group, and, when it represents an aralkyl group, it is preferably a C 7 to 10 aralkyl group, e.g. a benzyl group.

When $R^2$ represents a heterocyclyl group, it is preferably an oxygen, nitrogen or sulphur-containing heterocyclyl group, especially of 5 or 6 carbon atoms, for example furyl, especially 2-furyl, thienyl or pyridyl.

When $R^2$ represents a group $-S(O)_nR^5$, $R^5$ preferably represents C 1 to 4 alkyl, for example methyl, ethyl, n-propyl or t-butyl, phenyl or benzyl.

$R^3$ and $R^4$ are preferably both hydrogen or both alkyl, or one is hydrogen while the other is alkyl.

When $R^3$ and/or $R^4$ represents an alkyl group, it is preferably an alkyl group having from 1 to 12, especially 1 to 6, carbon atoms, for example methyl, ethyl, n-propyl, isopropyl, or isobutyl.

When $R^3$ and/or $R^4$ represents an aryl or aralkyl group, it is preferably unsubstituted. Preferred such groups are phenyl and benzyl.

When $R^3$ and/or $R^4$ represents an acyl group, that acyl group may be a substituted or unsubstituted alkanoyl group, preferably of 1 to 6 carbon atoms, which, if substituted, is preferably substituted by one or more halogen atoms (especially chlorine); for example acetyl or chloroacetyl, or an aroyl group, for example benzoyl. Preferred alkanesulphonyl groups which $R^3$ and/or $R^4$ may represent are those wherein the alkane moiety has from 1 to 6 carbon atoms, for example methanesulphonyl. Similarly, the preferred alkoxycarbonyl groups which one of $R^3$ and $R^4$ may represent are C 1 to 6 alkoxycarbonyl groups, for example methoxycarbonyl and ethoxycarbonyl.

When $R^3$ and/or $R^4$ represents an alkylated carbamoyl group, the alkyl group(s) thereof are preferably of 1 to 4 carbon atoms, e.g. methyl or ethyl. Particularly preferred alkylated carbamoyl groups which $R^3$ and/or $R^4$ may represent are methylcarbamoyl and dimethylcarbamoyl.

When $R^3$ and $R^4$, together with the nitrogen atom to which they are attached, form a heterocyclic ring system, that ring is preferably a 5- or 6-membered ring, for example pyrrolyl, morpholino, or piperidino.

When $R^3$ and $R^4$ together represent a group $=CR^8R^9$, and $R^8$ and/or $R^9$ represents an alkyl group, that alkyl group is preferably of 1 to 4 carbon atoms, e.g. methyl, ethyl or isopropyl. It is preferably unsubstituted. When, however, $R^8$ and/or $R^9$ represents a substituted alkyl group, the substituent(s) thereon are preferably halogen, e.g. chlorine, or alkoxy, e.g. methoxy. Specific substituted alkyl groups which $R^8$ and/or $R^9$ may represent are 2-chloroethyl and 2-hydroxyethyl.

When $R^8$ and/or $R^9$ represents a phenyl group, it is preferably unsubstituted. When, however, it represents a substituted phenyl group, it is preferably a nitro-, halo-, especially chloro-, alkyl-, especially methyl-, or alkoxy-, especially methoxy-, substituted phenyl group. Specific preferred substitued phenyl groups which $R^8$ may represent are 4-chlorophenyl, 3-nitrophenyl, 4-methylphenyl, and 2-methoxyphenyl. A particularly preferred group $=CR^8R^9$ is benzylidene.

Where $R^8$ and $R^9$ together with the carbon atom to which they are attached represent cycloalkyl, that cycloalkyl group is preferably of 3 to 7 carbon atoms, for example cyclopentyl or cyclohexyl.

When $R^8$ and/or $R^9$ represents heterocyclyl, it is preferably a 5- or 6-membered oxygen, nitrogen or sulphur-containing ring, especially 2-furyl.

The group $R^6$ preferably represents hydrogen. When, however, it represents an alkyl, alkenyl, cycloalkyl or alkynyl group, it is preferably such a group of up to 6 carbon atoms, for example methyl, ethyl, n-propyl, iso-propyl, allyl, cyclopentyl or cyclohexyl, or propargyl. When $R^6$ represents a substituted alkyl group, the substituent(s) therefrom are preferably halogen, e.g. chlorine, hydroxy or cyano.

When A represents $-C(OR^7)=N-$, the group $R^7$ is preferably C 1 to 6 alkyl, especially C 1 to 4 alkyl, for example methyl, ethyl n-propyl or iso-propyl.

Where $R^6$ represents a substituted alkyl group, the or each substituent thereon is preferably halogen, especially chlorine. Specific preferred such groups are chloromethyl and 2-chloroethyl.

A preferred group of compounds of formula I is that wherein $R^1$ represents hydrogen or an unsubstituted C 1 to 6 alkyl group, $R^2$ represents an unsubstituted or halogen-substituted C 1 to 6 alkyl group, a phenyl group or a furyl group, $R^3$ and $R^4$ represent hydrogen, alkyl of 1 to 4 carbon atoms, or acetyl, and $R^6$ or $R^7$ represents hydrogen, and the salts and acid addition salts thereof.

Particularly preferred compounds of formula I are those wherein $R^1$ represents an unsubstituted alkyl group of 1 to 4 carbon atoms especially methyl, ethyl, n-propyl or n-butyl, $R^2$ represents unsubstituted alkyl of 1 to 4 carbon atoms (especially methyl, ethyl, isopropyl or t-butyl), trifluoromethyl, phenyl or 2-furyl, $R^3$ represents hydrogen, methyl or acetyl, $R^4$ represents hydrogen or methyl, and $R^6$ or $R^7$ represents hydrogen, and the salts and acid addition salts thereof.

The preferred acid addition salts of the compounds of formula I are salts with mineral acids, such as sulphuric acid or the hydrogen halides, for example hydrochloric or hydrobromic acid, and organic acids, for example methanesulphonic acid and trifluoroacetic acid.

Salts of the pyrazolopyrimidines embraced by the present invention include ammonium salts, metal salts such as for example sodium, potassium, calcium, zinc, copper and magnesium salts, and amine salts such as for example those with methylamine, ethylamine, dimethylamine, triethylamine, ethanolamine, triethanolamine and benzylamine.

Specific preferred compounds of formula I are 2-methyl-3-amino-6-t-butyl-2,5-dihydropyrazolo[3,4-d]pyrimidin-4-one, 2-methyl-3-methylamino-6-t-butyl-2,5-dihydropyrazolo[3,4-d]pyrimidin-4-one, 2-methyl-3-dimethylamino-6-t-butyl-2,5-dihydropyrazolo[3,4-d]pyrimidin-4-one, 2-methyl-3-amino-6-ethyl-2,5-dihydropyrazolo[3,4-d]pyrimidin-4-one, 2-methyl-3-amino-6-phenyl-2,5-dihydropyrazolo[3,4-d]pyrimidin-4-one, 2-methyl-3-amino-6-isopropyl-2,5-dihydropyrazolo[3,4-d]pyrimidin-4-one, 2-methyl-3-amino-6-(2-furyl)-2,5-dihydropyrazolo[3,4-d]pyrimidin-4-one, 2-methyl-3-amino-6-trifluoromethyl-2,5-dihydropyrazolo[3,4-d]pyrimidin-4-one, 2-methyl-3-dimethylamino-6-trifluoromethyl-2,5-dihydropyrazolo[3,4-d]pyrimidin-4-one, 2-ethyl-3-amino-6-t-butyl-2,5-dihydropyrazolo[3,4-d]pyrimidin-4-one, 2-methyl-3-acetylamino-6-t-butyl-2,5-dihydropyrazolo[3,4-d]pyrimidin-4-one, and 2-n-butyl-3-amino-6-t-butyl-2,5-dihydropyrazolo[3,4-d]pyrimidin-4-one, and the salts and acid addition salts thereof.

It will be appreciated that the substituted pyrazolopyrimidines of formula I wherein $R^6$ represents hydrogen may exist in equilibrium with the tautomeric structure where A represents a group $-C(OH)=N-$ (i.e. a group A where $R^7$ represents hydrogen).

Further tautomeric structures naturally exist, and still further tautomeric structures exist when $R^2$ represents hydroxy.

This invention naturally extends to the compounds of formula I in the form of separate tautomers or as mixtures of those tautomers.

In another aspect, this invention provides a process for the preparation of compounds of formula I wherein A represents a group $-CONR^6-$, in which a 3-aminopyrazole of the formula:

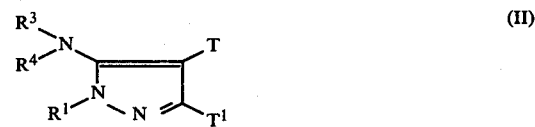

(where $R^1$, $R^3$ and $R^4$ are as hereinbefore defined, and T and $T^1$ represent a pair of groups cyclisable to form a chain $-CONR^6.CR^2=N-$) is cyclised to give the desired pyrazolopyrimidine of formula I.

The groups T and $T^1$ preferably respectively represent (a) $-CONHR^6$ or $-CN$ and $-NHCOR^2$, (b) $-CONHCOR^2$ or $-CONHCSR^2$ and $-NH_2$, or (c) $-CO_2R$ and $-NHC(=NH)R^2$, where $R^2$ and $R^6$ are as defined hereinbefore, and R represents alkyl.

The cyclisation may be effected by any method appropriate to the groups T and $T^1$. For example, when T and $T^1$ respectively represent the groups (a), (b) or (c) above, the cyclisation may be effected by heating, especially in an alkaline medium (to yield a salt) followed, if desired, by neutralisation (to yield the free compound). The alkaline medium is preferably an alkali-metal hydroxide, e.g. potassium or sodium hydroxide. The neutralising medium is preferably a mineral acid, e.g. hydrochloric acid.

The compounds of formula II may be prepared by a number of processes, in some of which, due to the conditions employed, they are believed to be prepared only transiently, since cyclisation occurs simultaneously to give a pyrazolopyrimidine of formula I wherein A represents a group -CONR⁶-.

Thus, for example, the compounds of formula II above where T and T¹ respectively represent groups -CONHR⁶ and -NHCOR², R² not being halogen or -S(O)$_n$R⁵, may be prepared by a process in which a 3,5-diaminopyrazole-4-carboxamide of the formula:

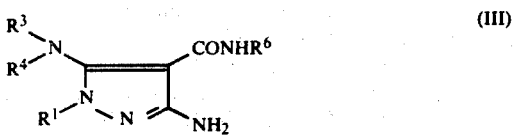

(where R¹, R³, R⁴ and R⁶ are as defined hereinbefore) is subjected to the action either of an acylating agent of formula R²COX (where R² is as defined hereinbefore but is not hydroxy or -S(O)$_n$R⁵, and X represents halogen, hydroxy, cyano or a group -O.COR²) or of an iminoester of formula

(where R² is as defined hereinbefore but is not hydroxy or -S(O)$_n$R⁵ and R represents alkyl).

The reaction is preferably effected by heating the reactants, and desirably in the presence of an organic base, e.g. pyridine.

When X represents halogen, as is preferred, it is conveniently chlorine or bromine. When R² in R²COX is halogen, the product is a compound in which R² represents hydroxy.

R in the iminoester preferably represents a C 1 to 4 alkyl group, e.g. methyl or ethyl.

The compounds of formula II above where T and T¹ respectively represent groups -CONH₂ and -NHCOR² may alternatively be prepared by a process in which a 3-amino-4-cyanopyrazole of the formula:

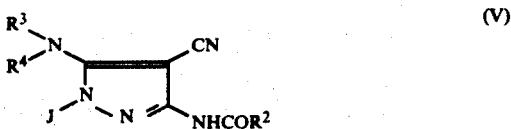

(wherein R², R³ and R⁴ are as defined hereinbefore and J represents either a group R¹ as defined hereinbefore, or a group -COR²) is subjected to the action of a base.

Where J represents a group -COR², the product of formula II is one in which R¹ represents hydrogen.

The base employed is preferably an alkali-metal base, for example sodium or potassium hydroxide, and the reaction therewith is desirably effected in an appropriate solvent medium, for example water.

The compounds of formula V where J represents a group R¹ are of course also compounds of formula II.

The compounds of formulae III wherein R⁶ represents hydrogen and V wherein R² is other than halogen or -S(O)$_n$R⁵ may themselves be prepared from compounds of the formula:

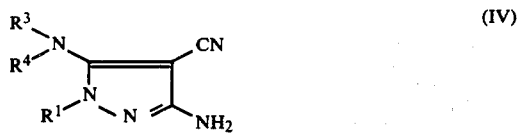

(wherein R¹, R³ and R⁴ are as defined hereinbefore) respectively by reaction with a base, especially an alkali-metal base, e.g. sodium or potassium hydroxide, to give the compounds of formula III, or by reaction with an agent of formula R²COX or with an iminoester of formula

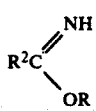

(where R², X and R are as defined hereinbefore but R² is other than hydroxy or -S(O)$_n$R⁵) to give compounds of formula V.

The reaction with the agent R²COX or the iminoester is preferably effected by heating, conveniently at reflux.

If desired, the compounds of formula V where J represents a group -COR² which differs from the group at the 3-position may be prepared by reaction first with one molar proportion of an agent R²COX, followed by reaction with one molar proportion of a second agent R²COX wherein the group R² is different to that first employed.

The compounds of formula II above where T and T¹ respectively represent groups -CONHCOR² or -CONHCSR² and -NH₂ may be prepared by a process in which a substituted acetamide of the formula M¹C(CN)₂ CONH.COR² or M¹.C(CN)(CONH₂)CONH.COR², or M¹C(CN)₂.CONH.C$^S$R² or M¹C(CN)(CONH₂)CONH.CSR², (where R² is as defined hereinbefore, and M¹ represents hydrogen or a metal, especially an alkali-metal, e.g. potassium) is reacted with a substituted hydrazine of the formula R¹NHNH₂ (where R¹ is as defined hereinbefore) to give the desired compound of formula II.

The compounds of formula II in which T and T¹ respectively represent -CO₂R and -NHC(=NH)R² may be prepared from the corresponding compounds where the groups respectively represent -CO₂R and -NH₂ by reaction with a compound of formula R²CN or R²C(=NH)NH₂.

The reaction is desirably effected in an appropriate solvent medium, e.g. water. Where M¹ represents a metal, the reaction is desirably carried out in the presence of an acid, e.g. hydrochloric acid.

The compounds of formulae III and IV may themselves be prepared by a process in which a compound of the formula:

(wherein R¹, R³ and R⁴ are as defined hereinbefore, E represents

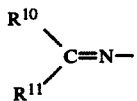

or $R^{10}CONH-$ where $R^{10}$ represents a substituted or unsubstituted alkyl or aryl group, and $R^{11}$ represents hydrogen or a substituted or unsubstituted alkyl or aryl group, and Y represents either cyano, to give compounds of formula IV, or a group $-CONHR^6$ where $R^6$ is as defined hereinbefore, to give compounds of formula III) is subjected to the action of an acid to give the desired compound of formula III or formula IV.

The reaction is desirably effected in an appropriate solvent medium, e.g. water.

The acid employed is preferably a mineral acid, for example a hydrohalic acid, e.g. hydrochloric acid.

$R^{11}$ preferably represents hydrogen. $R^{10}$ conveniently represents phenyl.

The compounds of formula VI may themselves be prepared by reaction of a compound of formula:

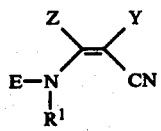

(where $R^1$, E and Y are as defined hereinbefore, and Z represents a good leaving group) with an amine of formula $R^3R^4NH$ (where $R^3$ and $R^4$ are as defined hereinbefore) to give the desired compound of formula VI.

The reaction is desirably effected in a high boiling point solvent medium, for example 2-methoxyethanol.

Z may be any convenient leaving group, but is preferably an alkylthio or alkoxy group, e.g. methylthio or ethoxy.

The compounds of formula VII may themselves be prepared by reaction of a compound of formula:

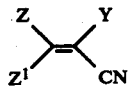

(wherein Z and Y are as defined hereinbefore, and $Z^1$ represents a good leaving group) with a hydrazone or hydrazide of the formula

 E.NHR$^1$ (IX)

(wherein E and $R^1$ are as defined hereinbefore) to give the desired compound of formula VII.

The reaction is desirably effected by heating in an appropriate solvent.

The solvent employed is preferably an alkanol, e.g. 2-methoxyethanol or ethanol.

$Z^1$ Preferably represents a leaving group identical to Z.

The compounds of formulae III and IV wherein $R^1$ represents hydrogen may alternatively be prepared by a process in which a compound of the formula:

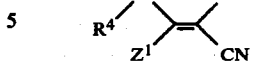

(wherein $R^3$, $R^4$, Y and $Z^1$ are as defined hereinbefore) is reacted with hydrazine to give the desired compound of formula III or IV.

The reaction is conveniently effected by heating in an appropriate solvent, e.g. water.

The compounds of formula X may be prepared by a process in which a compound of formula VIII is reacted with an amine of formula $R^3R^4NH$.

This reaction is preferably effected by heating in an appropriate solvent, e.g. water, or an alkanol, e.g. methanol.

The compounds of formula IV wherein $R^3$ and $R^4$ represent hydrogen may alternatively be prepared by a process in which a substituted hydrazine of the formula $R^1NHNH_2$ (wherein $R^1$ is as defined hereinbefore) or an acid salt-thereof is reacted in a neutral or acid medium with tricyanomethane or an alkali-metal salt thereof to give the desired compound of formula IV. Where an alkali-metal salt of tricyanomethane is employed, it is preferably reacted with an acid salt of the substituted hydrazine.

The alkali-metal tricyanomethanide is preferably potassium tricyanomethanide ($KC(CN)_3$).

The medium employed is preferably water, which may contain a mineral acid, such as a hydrogen halide, for example hydrochloric acid.

The 3,5-diaminopyrazole-4-carboxamides of formula III wherein $R^3$ and $R^4$ represent hydrogen may be prepared by a process in which a dicyanoacetamide of the formula $HC(CN)_2CONHR^6$, where $R^6$ is as defined hereinbefore, or a salt thereof, is reacted in an acid or neutral medium with a substituted hydrazine of the formula $R^1NH.NH_2$ (wherein $R^1$ is as defined hereinbefore) to give the desired compound of formula III.

In a preferred method, the substituted hydrazine and the dicyanoacetamide are heated together in an aqueous medium at a pH of from 1 to 7. The dicyanoacetamide may be generated in situ from a salt thereof by means of a mineral acid.

When a salt of dicyanoacetamide is employed, it is preferably an alkali-metal salt thereof, for example the potassium salt.

The compounds of formula $M^1C(CN)_2.CONH.COR^2$, $M^1C(CN)(CONH_2).CONH.COR^2$, $M^1C(CN)_2.CONH.CSR^2$ and $M^1C(CN)(CONH_2)CONH.CSR^2$ employed as starting materials in the preparation of certain compounds of formula II may themselves be prepared by a process in which an isocyanate of formula $R^2CO.NCO$ or $R^2CS.NCO$ is reacted with dicyanomethane or cyanoacetamide, as appropriate, in the presence of $M^1OH$ (where $M^1$ is as defined hereinbefore).

The compounds of formulae II, III, IV and V may be converted into other compounds of the same formula by methods well known to those skilled in organic synthesis. For example, where $R^1$ in a compound of formula II, III, IV and V, especially in a compound of formula IV, represents hydrogen, the corresponding compound where $R^1$ represents alkyl may be prepared by alkylation thereof, e.g. employing a dialkyl sulphate or an alkyl iodide in the presence of a base, e.g. potassium carbonate.

Furthermore, the compounds of formulae II, III, IV and V may be converted into corresponding compounds of another of those formulae by methods which will be familiar to those skilled in organic synthesis.

Examples of interconversions which may be effected are as follows:

(a) the compounds of formula IV may be prepared by a process in which a compound of formula III is dehydrated by means of an appropriate dehydrating agent, e.g. phosphorus pentoxide;

(b) the compounds of formula IV may be prepared by a process in which a compound of formula V is treated with an aqueous acid, e.g. sulphuric acid;

(c) compounds of formula V may be prepared by a process in which a compound of formula II wherein $R^6$ represents hydrogen is reacted with a carboxylic acid anhydride;

(d) the compounds of formula III may be prepared by a process in which a compound of formula II wherein T and $T^1$ respectively represent —$CONHR^6$ or —CN and —$NHCOR^2$ is treated with an aqueous acid, e.g. sulphuric acid.

In another aspect, this invention provides a process for the preparation of compounds of formula I in which a pyrimidine of the formula:

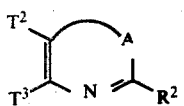
(XX)

(wherein A and $R^2$ are as defined hereinbefore and $T^2$ and $T^3$ represent a pair of groups cyclisable to form a chain

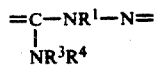

is cyclised to give the desired pyrazolopyrimidine of formula I.

The groups $T^2$ and $T^3$ preferably respectively represent the pairs of groups —CN and $R^1NHNH$— or —$CONR^3R^4$ and $R^1NHNH$—, where $R^1$, $R^3$ and $R^4$ are as defined hereinbefore.

The cyclisation may be effected by any method appropriate to the groups $T^2$ and $T^3$. For example when $T^2$ and $T^3$ respectively represent the groups —CN and $R^1NHNH$— or —$CONR^3R^4$ and $R^1NHNH$—, the cyclisation may be effected by heating in an appropriate solvent, optionally, in the presence of a base (to give a salt of the desired compound).

The compounds of formula XX may be prepared by a number of processes, in some of which, due to the conditions employed, they are believed to be prepared only transiently, since cyclisation occurs simultaneously to give a pyrazolopyrimidine of formula I.

Thus, for example, the compounds of formula XX where $T^3$ represents a group $R^1NHNH$— may be prepared by a process in which a compound of formula:

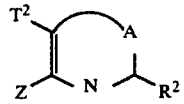
(XXI)

(where $R^2$, A and $T^2$ are as defined hereinbefore, and Z represents a leaving group) is reacted with an amine of the formula $R^1NH.NH_2$ (where $R^1$ is as defined hereinbefore) to give the corresponding compound of formula XX.

Z may represent any convenient leaving group, but preferably represents methylthio or chloro.

The reaction is preferably effected by heating in an appropriate solvent.

The compounds of formula XXI where A represents —CONH— and $R^2$ is other than halogen or -$S(O)_nR^5$ may be prepared by a process in which a compound of formula:

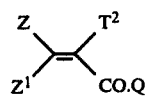
(XXII)

(where $T^2$ and Z are as defined hereinbefore, $Z^1$ represents a leaving group the same as or different from Z, and Q represents alkoxy or amino) is reacted with a compound of formula:

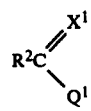
(XXIII)

(where $R^2$ is as defined hereinbefore but is other than hydroxy or -$S(O)_nR^5$, $X^1$ represents =O or =NH and $Q^1$ represents alkoxy or amino the same as or different from Q, at least two of $X^1$, Q and $Q^1$ representing nitrogen-containing groups) to give the desired compound of formula XXI.

$Z^1$ preferably represents the same leaving group as Z.

When Q or $Q^1$ represents an alkoxy group, it is preferably a C 1 to 4 alkoxy group, e.g. methoxy or ethoxy.

The reaction is desirably effected by heating in an appropriate solvent.

The compounds of formula XXI wherein A represents -$C(OR^7)$=N-may be prepared from the corresponding compounds wherein A represents -CONH- by methods analogous to those described hereinafter in connection with the compounds of formula I.

In a further aspect, this invention provides a process for the preparation of compounds of formula I wherein $R^3$ and $R^4$ both represent hydrogen, in which a 3-nitropyrazolopyrimidine of the formula:

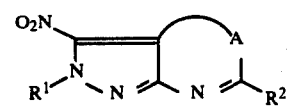
(XXX)

(wherein $R^1$, $R^2$ and A are as defined hereinbefore) is reduced to give the corresponding compound of formula I wherein $R^3$ and $R^4$ represent hydrogen.

The reduction is conveniently effected by means of an appropriate reducing agent, e.g. tin or iron and hydrochloric acid, preferably in an alkanol/water solvent medium.

The nitropyrazolopyrimidines of formula XXX above may themselves be prepared by a process in which a compound of the formula:

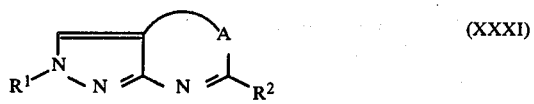

(wherein $R^1$, $R^2$ and A are as defined hereinbefore) is nitrated to give the desired compound.

The nitration is conveniently effected by means of a nitric acid/sulphuric acid mixture under conventional conditions.

In a yet further aspect, this invention provides a process for the preparation of compounds of formula I in which a pyrazolopyrimidine of the formula:

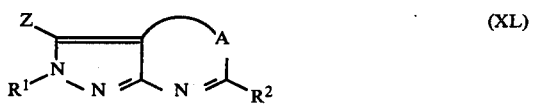

(wherein $R^1$, $R^2$, A and Z are as defined hereinbefore) is reacted with an amine of formula $R^3R^4NH$ (where $R^3$ and $R^4$ are as defined hereinbefore) in an appropriate solvent medium to give the desired compound of formula I.

The leaving group Z may be any convenient leaving group. Preferably, however, it is a diazo group or a group $RS(O)_n$ (where R is as defined hereinbefore and n represents 0, 1 or 2), e.g. methylthio or ethylthio, or halo, e.g. chloro or bromo.

The solvent medium employed is preferably an ether, for example 2-methoxyethanol, or tetrahydrofuran.

The compounds of formula XL which are themselves novel, may be prepared from the corresponding compounds of formula I where $R^3$ and $R^4$ represent hydrogen by diazotization to give a diazo leaving group at the 3-position, followed if desired by reaction with a compound containing a different leaving group Z.

In another aspect, this invention provides a process for the preparation of an unsalified compound of formula I, in which a salt of a compound of formula I is subjected to the action of one molar proportion of an acid to give the desired compound.

The compounds of formula I wherein A represents a group $-C(OR^7)=N-$ where $R^7$ is other than hydrogen may be prepared from the corresponding compounds where $R^7$ represents hydrogen (i.e. compounds tautomeric with those wherein A represents a group -CO-NH-) by alkylation thereof, or by reaction thereof by methods well known to those skilled in organic synthesis to yield the corresponding compound where the -OH group is replaced by a leaving group Z as defined hereinbefore (such compounds being novel), followed by reaction thereof with an alkoxide of formula $R^7OM$ where M is an alkali-metal and $R^7$ is a substituted or unsubstituted alkyl group, to give the desired compound of formula I.

The good leaving group is preferably a chlorine or bromine atom, and suitable reagents for the introduction thereof will be apparent to those skilled in organic synthesis. Suitable reagents include phosphorus pentachloride, phosphorus trichloride, phosphorus oxychloride, phosphorus pentabromide, and thionyl chloride/dimethylformamide.

The subsequent reaction with the alkoxide $R^7OM$ is preferably performed in a solvent, which is conveniently of the formula $R^7OH$ corresponding to the alkoxide employed.

The compounds of formula I may also be converted into other compounds of formula I by methods well-known to those skilled in organic synthesis.

For example, the compounds of formula I wherein $R^3$ and/or $R^4$ represents other than hydrogen may be prepared from the corresponding compounds of formula I wherein $R^3$ and/or $R^4$ represents hydrogen by known processes for such conversions.

Thus, the compounds of formula I wherein $R^3$ and/or $R^4$ represents alkyl may be prepared for example by reaction of the corresponding compound of formula I wherein $R^3$ and/or $R^4$ represents hydrogen with an alkyl halide, for example methyl iodide, in the presence of a base, for example an alkali-metal base, e.g. potassium carbonate.

Similarly, the compounds of formula I wherein $R^3$ and/or $R^4$ represents acyl, alkanesulphonyl, alkoxycarbonyl, carbamoyl or alkylated carbamoyl may be prepared for example by reaction of the corresponding compound of formula I wherein $R^3$ and $R^4$ represent hydrogen, with reagents containing the desired $R^3$ and $R^4$ groups by methods well-known to those skilled in organic synthesis.

The compounds of formula I wherein $R^3$ and $R^4$ form, together with the nitrogen atom to which they are attached, a heterocyclic ring system may be prepared from the corresponding compound of formula I where $R^3$ and $R^4$ represent hydrogen by reaction with an $\alpha,\omega$-dibromoalkane.

The compounds of formula I wherein $R^3$ and $R^4$ together form a group $=CR^8R^9$ may be prepared from the corresponding compounds of formula I wherein $R^3$ and $R^4$ represent hydrogen by reaction thereof with an aldehyde or ketone of formula $R^8R^9CO$.

The reaction is preferably effected by heating the reactants.

The compounds of formula I wherein $R^2$ represents halogen may be prepared from the corresponding compounds where $R^2$ represents hydroxy by well-known halogenation techniques, e.g. by reaction with phosphorus oxychloride.

The compounds of formula I wherein $R^2$ represents $-S(O)_nR^5$ where n=0 may be prepared from the corresponding compounds where $R^2$ represents halogen by reaction with $R^5SH$, and the compounds where n=1 or 2 may be prepared from those in which n=0 by oxidation with hydrogen peroxide.

The compounds of formula I wherein $R^6$ represents alkyl, cycloalkyl, amino, alkylamino or dialkylamino may be prepared from the corresponding compounds of formula I wherein $R^6$ represents hydrogen by methods well-known to those skilled in organic synthesis.

Salts of the compounds of formula I may be prepared by reaction of the corresponding unsalified compound of formula I with an appropriate base, e.g. an alkalimetal base, e.g. sodium or potassium hydroxide.

The acid addition salts of the compounds of formula I may be prepared by reaction of the corresponding free compound of formula I with the appropriate acid to form the desired salt.

The unsalified compounds of formula I may be prepared by reaction of an acid addition salt thereof with one molar proportion of a base, or by reaction of a salt thereof with one molar proportion of an acid.

The invention naturally extends to the compounds of formula I and the salts and acid addition salts thereof whenever prepared by a process as described herein.

The compounds of formula II, the 3,5-diaminopyrazole-4-carboxamides of the formula III, the 3,5-diamino-4-cyanopyrazoles of formula IV (except where $R^1$, $R^3$ and $R^4$ all represent hydrogen), the 3-amido-4-cyano-5-aminopyrazoles of formula V, the compounds of formulae VI and VII, the compounds of formulae XX, XXI, XXX and XL as defined herein are themselves novel compounds, and this invention provides them per se, as well as processes for their preparation as described herein. The other starting materials employed are either known compounds or may be prepared by methods well-known to those skilled in organic synthesis for the preparation of analogous compounds.

The compounds of formula I and their salts and acid addition salts are herbicidally active, and may be used as selective herbicides.

Accordingly, in another aspect, this invention provides a method of combating weeds at a locus either infested or liable to infestation therewith, which comprises applying to said locus an effective amount of one or more compounds of formula I or salts or acid addition salts thereof.

In a further aspect, this invention provides a herbicidal composition comprising one or more compounds of formula I or a salt or acid addition salt thereof in association with a suitable carrier and/or surface active agent.

The compositions will normally be produced initially as formulations containing from 0.5 to 99%, preferably from 0.5 to 85% by weight, more usually from 10 to 50% by weight, of the active ingredient, which are diluted if necessary before application to the locus to be treated such that the concentration of active ingredient in the formulation applied is from 0.05 to 5% by weight.

The carrier may be a liquid, e.g. water (e.g. water used to dilute a concentrate for application). If water is employed as carrier in a concentrate, an organic solvent may also be present as carrier, though this is not usually employed. A concentrate containing water as carrier may advantageously also contain a surface active agent.

These compounds soluble in water may be used as aqueous solutions with or without a surface active agent.

The carrier may be a liquid other than water, for example an organic solvent, usually a water-immiscible solvent, e.g. a hydrocarbon which boils within the range 130°-270° C., in which the essential herbicides are dissolved or suspended. A concentrate containing an organic solvent suitably also contains a surface active agent so that the concentrate acts as a self-emulsifiable oil on admixture with water.

The carrier is preferably however a solid, which may be finely divided. Examples of suitable solids are limestone, clays, sand, mica, chalk, attapulgite, diatomite, perlite, sepiolite, silicas, silicates, lignosulphonates and solid fertilizers. The carrier can be of natural or synthetic origin or can be a modified natural material.

Wettable powders soluble or dispersable in water may be formed by admixing the essential herbicides in particulate form with a particulate carrier or spraying molten compound onto the particulate carrier, admixing a wetting agent and a dispersing agent therewith and finely grinding the whole powder mixture.

An aerosol composition may be formed by admixing the compound with a propellant, e.g. a polyhalogenated alkane, such as dichlorodifluoromethane, and suitably also with a solvent.

A flowable suspension concentrate may be formed by grinding the active ingredient with water, a wetting agent and a suspending agent.

Thus, the present compositions may for example be solid (e.g. dust or granules) and contain a solid carrier, or liquid (e.g. an emulsifiable concentrate) and contain a liquid carrier.

The term 'surface active agent' is used in the broad sense to include materials variously called emulsifying agents, dispersing agents and wetting agents. Such agents are well known in the herbicide art.

The surface active agents used may comprise anionic surface active agents, for example mono- or di-esters of phosphoric acid with fatty alcohol ethoxylates or salts of such esters, fatty alcohol sulphates such as sodium dodecyl sulphate, ethoxylated fatty alcohol sulphates, ethoxylated alkylphenol sulphates, lignin sulphonates, petroleum sulphonates, alkylaryl sulphonates such as alkyl-benzene sulphonates or lower alkyl-naphthalene sulphonates, salts of sulphonated naphthalene-formaldehyde condensates, salts of sulphonated phenol-formaldehyde condensates, or more complex sulphonates such as the amide sulphonates, e.g. the sulphonated condensation product of oleic acid and N-methyl taurine or the dialkyl sulphosuccinates e.g. the sodium sulphonate of dioctyl succinate.

The surface active agents may also comprise non-ionic agents, for example condensation products of fatty acid esters, fatty alcohols, fatty acid amides or alkyl-substituted phenols with ethylene oxide, fatty esters of polyhydric alcohol ethers e.g. sorbitan fatty acid esters, condensation products of such esters with ethylene oxide e.g. polyoxyethylene sorbitan fatty acid esters, block copolymers of ethylene oxide and propylene oxide, acetylenic glycols such as 2,4,7,9-tetramethyl-5-decyn-4,7-diol, or ethoxylated acetylenic glycols.

The surface active agents may also comprise cationic agents, for example alkyl- and/or aryl-substituted quarternary ammonium compounds such as cetyl trimethylammonium bromide, or ethoxylated tertiary fatty amines.

Preferred surface active agents include ethoxylated fatty alcohol sulphates, lignin sulphonates, alkyl-aryl sulphonates, salts of sulphonated naphthalene-formaldehyde condensates, salts of sulphonated phenol-formaldehyde condensates, sodium oleoyl N-methyltauride, dialkyl sulphosuccinates, alkyl phenol ethoxylates, and fatty alkyl ethoxylates.

The compounds of the present invention, especially those specifically identified herein, and particularly 2-methyl-3-amino-6-t-butyl-2,5-dihydropyrazolo[3,4-d]pyrimidin-4-one or 2-methyl-3-amino-6-trifluoromethyl-2,5-dihydropyrazolo[3,4-d]pyrimidin-4-one or the 3-dimethylamino analogues of either, may be admixed with one or more additional pesticides, e.g. herbicides, insecticides or fungicides, or with one or more plant growth regulants or fertilizers. Particular advantages are obtained with mixtures with a second herbicide or herbicidal mixture.

The compounds of the present invention may also advantageously be employed sequentially with a second herbicide, with one herbicide being employed before the other, e.g. one herbicide being employed before planting or before emergence of the crop and the other herbicide being employed after emergence of the crop.

Alternatively, a mixture of a compound of the present invention and another herbicide may be applied to the locus, followed later by another mixture of a compound of the present invention and a another herbicide, each admixture being applied in a sub-phytotoxic amount. Preferably the first and second admixtures are the same, and are applied in similar amounts. Greater than additive effects are often observed.

The second herbicide employed in admixture or sequentially with the compounds of the present invention is very preferably a substituted benzofuran herbicide, since such admixtures appear in general to be synergistic, but may alternatively be, for example, a phenoxyaliphatic acid, substituted urea, triazine, phenol, nitrile, bipyridylium compound, substituted benzoic acid, halogenated aliphatic acid, carbamate, thiocarbamate, chloroacetamide, diazine, arsenic compound or other herbicidal compound. In respect of selective herbicidal compositions for post-emergence use, the second herbicide is preferably a substituted phenoxyaliphatic acid; in respect of selective herbicidal compositions for pre-emergence use, the second herbicide is preferably a substituted benzofuran, a substituted urea or triazine.

The substituted benzofuran herbicide is preferably a compound of the formula:

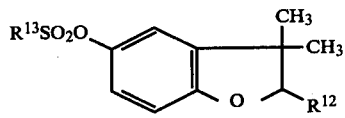

where $R^{12}$ represents alkoxy (especially ethoxy, propoxy or isopropoxy), and $R^{13}$ represents alkyl (especially methyl) or a group $R^{14}R^{15}N-$ where $R^{14}$ and $R^{15}$, which may be the same or different, each represent hydrogen, alkyl (especially methyl) or carboxylic acyl (especially acetyl).

Particularly preferred substituted benzofuranyl compounds for admixture with the compounds of the present invention, especially with those specifically identified herein, and particularly with 2-methyl-3-amino-6-t-butyl-2,5-dihydropyrazolo[3,4-d]pyrimidin-4-one or 2-methyl-3-amino-6-trifluoromethyl-2,5-dihydropyrazolo[3,4-d]pyrimidin-4-one, or the 3-dimethylamino analogue of either, are:

2-ethoxy-2,3-dihydro-3,3-dimethylbenzofuran-5-yl methanesulphonate (common name ethofumesate);

2-ethoxy-2,3-dihydro-3,3-dimethylbenzofuran-5-yl methylsulphamate; and 2-ethoxy-2,3-dihydro-3,3-dimethylbenzofuran-5-yl dimethylsulphamate.

The phenoxyaliphatic acid generally comprises alkyl and/or halogen substituted phenoxyaliphatic acids, and their salts, for example alkali metal, amine and alkanolamine salts, and functional derivatives, for example esters and amides. These compounds may be of activity such that they are recognised as commercial herbicides, or may be of only slight herbicidal activity.

The substituted urea generally comprises a tri- or tetrasubstituted urea.

The triazine herbicide generally comprises a compound of the formula:

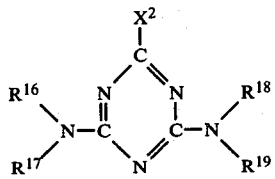

where $X^2$ is a halogen, $OY^1$ group or $SY^1$ group, where $Y^1$ is an alkyl group, and $R^{16}$, $R^{17}$, $R^{18}$, $R^{19}$ are hydrogen or alkyl.

Specific compounds with which the compounds of the present invention, especially those specifically identified herein, and particularly 2-methyl-3-amino-6-t-butyl-2,5-dihydropyrazolo[3,4-d]pyrimidin-4-one or 2-methyl-3-amino-6-trifluoromethyl-2,5-dihydropyrazolo[3,4-d]pyrimidin-4-one may be admixed or employed sequentially are as follows, all common names being as set out in the Pesticide Manual, 4th edition, issued by the British Crop Protection Council:

alachlor, allidochlor, ametryne, aminotriazole (ATA), ancymidol, asulam, atrazine, aziprotryne, barban, benazolin, benfluralin, bensulide, bentazon, benthiocarb, bentranil, benzadox, benzoylpropethyl, benzthiazuron, bifenox, bromacil, bromofenoxim, bromoxynil, bromoxynil octanoate, brompyrazone, butachlor, buturon, butylate, cabetamide, chinonamid, chloramben, chloranocryl, chlorburomuron, chlorbufam, chlorfenac, chlorfenprop-methyl, chlorflurecol-methyl, chlormequat, chloroxuron, chlorphonium, chlorpropham, chlorthaldimethyl, chlorthiamid, chlortoluron, credazine, cyanazine, cycloate, cycluron, cyprazine, 2,4-D, dalapon, dalapon sodium, daminozide, 2,4-DB, delachlor, desmedipham, desmetryne, diallate, dicamba, dichlobenil, dichlorprop, dimethametryn, difenzoquat, difenzoquat methylsulphate, dimexan, dinitramine, dinoseb, dinoseb acetate, dinoterb, dinoterb acetate, diphenamid, dipropetryn, diquat, diuron, DNOC, DSMA, endothal, EPTC, erbon, ethiolate, EXD, fenoprop, fenuron, flamprop-isopropyl, fluometuron, fluorodifen, flumezin, flurecol-butyl, glyphosate, hexaflurate, ioxynil, ioxynil octanoate, isonoruron, isopropalin, isoproturon, karbutilate, lenacil, linuron, MCPA, MCPB, mecoprop, medinoterb acetate, merphos, methabenzthiazuron, methazole, methoprotryne, metobromuron, metoxuron, metribuzin, molinate, monalide, monolinuron, monuron, monuron-TCA, MSMA, napropamide, naptalam, neburon, nitralin, nitrofen, norflurazon, noruron, oryzalin, paraquat, pebulate, pentanochlor, phenmedipham, phenmedipham-ethyl, phenobenzuron, picloram, piperophos, profluralin, prometon, prometryne, propachlor, propanil, propazine, propham, propyzamide, pyrazon, secbumeton, siduron, simazine, simetryne, sulfallate, swep, 2,4,5-T, 2,3,6-TBA, TCA, terbacil, terbucarb, terbumeton, terbuthylazine, terbutryne, thiafluron, triallate, trietazine, trifluralin, and vernolate, N-(α,α-dimethylbenzyl)-N'-p-tolylurea, 3,4,5-tribromo-N,N-dimethylpyrazole-1-acetamide (U 27267), N-methyl-N-cyclohexyldithio-N'-o-fluorophenyl urea, N-benzoyl-N-(3,4-dichlorophenyl)-N',N'-dimethyl urea, ethyl-N,N-diisobutylthiolcarbamate, 4-(methylsulphonyl)-2,6-dinitro-N,N-dipropylaniline, 5-(6)-chloro-2-isopropylbenzimidazole, 1-(3,4-dichlorophenyl)-3-methyl-2-pyrrolidinone, N-(p-bromophenyl-N'-methyl-N'-methoxyurea, 3-(2,4-dichlorophenyl)-5-t-butyl-1,3,4-oxadiozol-2-one, N-

(3,4-dichlorophenyl)-cyclopropanecarboxamide, 2,3,5-trichloro-4-pyridinol, 2-chloro-isopropylacetanilide, 2,6-dichlorothiobenzamide, 1,1′-bis(3,5-dimethylmorpholinocarbonylmethyl)-4,4′-bipyridilium, dichloride, sodium cis-3-chloroacrylate, 4,5,7-trichlorobenzthiadiazole-2,1,3, N-(3-chloro-4-methylphenyl)-2-methylpentanamide, n-propyl ethyl-n-butylthiolcarbamate, 3,4-dichloropropionanilide, N-cyclooctyl-N′,N′-dimethylurea, butyl m-chlorophenylcarbamate, 2-chloro-N-(1,3-dioxolan-2-ylmethyl)-2′,6′-dimethylacetanilide, tetrahydrofurfuryl isothiocyanate, N-chloroacetyl-N-(2,6-diethylphenyl)-glycine isopropyl ester, N-chloroacetyl-N-(2,6-diethylphenyl)-glycine ethyl ester, N-chloroacetyl-N-(2-methyl-6-ethylphenyl)-glycine isopropyl ester, (1-methylethyl)-O-methyl-O-(4-methyl-2-nitrophenyl)-phosphoramidothioate, 1,1-dimethylhexahydropyridazinum bromide, dimethylpiperidinium chloride, 1-[2-(2,4-dichlorophenyl)-1,3-dioxolan-2-methyl]imidazole, 3′-(trifluoromethyl)-phthalanilic acid, 3,6-dichloropicolinic acid, benzyl-3,5-dichloro-2,6-difluoro-4-pyridyl ether, ethyl-N-(2,4-dichlorophenyl)-N-(trifluoromethanesulphonyl)-carbamate, N-(p-chlorophenyl)-N-(trifluoromethanesulphonyl)-carbamate, N-(p-chlorophenyl)-3,4,5,6-tetrahydrophthalimide, tributyl-[(5-chloro-2-thienyl)-methyl]-phosphonium chloride, N-pyrrolidinosuccinamic acid, methyl-3,6-dichloro-o-anisole, ethyl-5-(4-chlorophenyl)-2-H-tetrazol-2-yl acetate, 2-(4-ethylamino-6-methylthio-s-triazin-2-yl)-amino-2-methylpropionitrile, 3-cyclohexyl-(6-dimethylamino)-1-methyl-1,3,5-triazine-2,4-(1H,3H)-dione, 1-(N-ethyl-N-propylcarbamoyl)-3-propyl-sulphonyl-1H-1,2,4-triazole, N-ethyl-N-(2-methyl-2-propenyl)-2,6-dinitro-4-(trifluoromethyl)-benzenamine, 2-ethyl-6-methyl-N-(1′-methyl-2′-methoxyethyl)-chloro-acetanilide, 2-(3-chlorophenoxy)-propionic acid, N-n-propyl-N-cyclopropylmethyl-4-trifluoromethyl-2,6-dinitroaniline, N-benzyl-N-isopropyl-3,5-dimethylbenzamide, N-phenyldiethanolamine-bis(2-methoxy-3,6-dichlorobenzoate), [(3,5,6-trichloro-2-pyridinyl)oxy]-acetic acid, 3,3a-dihydro-2-(p-methoxyphenyl)-8H-pyrazolo-(5,1a)-isoindol-8-one, cis-2-ethyl-5-methyl-5-(2-methylbenzyloxy)-1,3-dioxane, 3-(1-N-ethoxyamino)-propyliden-6-ethyl-3,4-dihydro-2H-pyran-2,4-dione, N-(5-n-butylsulphonyl-1,3,4-thiadiazolyl)-N,N′-dimethyl urea, 1,1-dimethyl-3-(m-chloro-p-trifluoromethoxyphenyl)-urea, 2,6-dimethyl-N-2′-methoxyethylchloracetanilide, 1-(2-α,α-dimethylbenzyl)-3-methyl-3-phenyl urea, 1-(o-fluorophenyl)-3-methyl-5-iminohydantoin, N-methyl-N-2-chlorocyclohexylthio-N′-2-fluorophenyl urea, 1-(3,4-dichlorophenyl)-3-methyl-3-(1-formyloxy-2,2,2-trichloroethyl)-urea, N-methyl-N-cyclohexyldithio-N′-o-fluorophenyl urea, N-carboxymethoxymethyl-2,6-diethyl-chloroacetamide, 6-t-butyl-4,5-dihydro-3-isopropylpyrimidino-[4,5-c]isothiazol-4-one, 6-t-butyl-4,5-dihydro-3-isopropyrimidino-[5,4-d]-isoxazol-4-one, O-(5-chloro-1-isopropyl-1,2,4-triazol-3-yl)-O,O-diethylphosphorothioate, 2,4-dichlorophenyl-3-methoxy-4-nitrophenyl ether, 2-ethyl-5-methyl-5-(2-methylbenzyloxy)-1,3-dioxan, N-(1-ethylpropyl)-2,6-dinitro-3,4-xylidine, hexafluoroacetone trihydrate, methyl-tetrachloro-N-methoxy-N-methylterephthalamate, S,S,S-tributyl phosphorotrithioate, N-sec-butyl-2,6-dinitro-3,4-xylidine, N,N-dimethyl-2-(3,4,5-tribromo-1-pyrazolyl)-propionamide, α-(2,2,2-trichloroethyl)-styrene, 2-isopropyl-5-methyl-5-(2-methylbenzyloxy)1,3-dioxane, 1-[O-methyl-sulphamoyl-1-glycol]-hexahydroazepin, O-(methylsulphamoyl)-N,N-hexamethyleneglycollamide, O-(methylsulphamoyl)-glycol-N-isopropylanilide, O-(methylsulphamoyl)-N-isopropylglycollanilide, isobutyl 2-[4-(4-chlorophenoxy)-phenoxy]-propionate, methyl 2-[4-(2,4-dichlorophenoxy)-phenoxy]-propionate, 6-chloro-2-trifluoromethylimidazo(4,5-b)pyridine, pentachlorophenol, N′-p-chlorophenyl-O,N,N-trimethylisourea, 2-chloro-N-(but-1-yn-3-yl)-acetanilide, 2-bromo-2′-methyl-6′-t-butylacetanilide, 2-bromo-N-(methoxymethyl)-2′-methyl-6′-t-butyl-acetanilide, 2-chloro-N-(ethoxycarbonyloxymethyl)-2′,6′-diethyl-acetanilide, O-(isopropylsulphamoyl)-N-(but-1-yn-3-yl)-glycollanilide, ethyleneglycol bis-(trichloroacetate), hexachloroacetone, potassium cyanate, sodium chlorate, sodium metaborate, trichlorobenzyl chloride, undecylenic acid, N-(1-ethylpropyl)-3,4-dimethyl-2,6-dinitrobenzeneamine, tris(2-methoxyethoxy)-2′-chloroethylsilane, N-[2,4-dimethyl-5[[(trifluoromethyl)-sulphonyl]-amino]-phenyl]-acetamide, 6-t-butyl-4-isobutylideneamino-3-methylthio-1,2,4-trazin-5(4H)-one, 2[4-(2′,4′-dichlorobenzyl)-phenoxy]-propionic acid, methyl ester, S-(4-methoxybenzyl-N,N-diethylcarbamothioate, 2-chloro-1-(3-ethoxy-4-nitrophenoxy)-4-trifluoromethylbenzene, 3-(3-chloro-4-trifluoromethoxyphenyl)-1,1-dimethyl urea, N-isobutyl-2-oxoimidazolidine-1-carboxamide, O-ethyl-O-(3-methyl-6-nitrophenyl)-N-sec-butyl-phosphorthioamidoate, N-isobutyl-2-oxo-1-imidazolidene carboxamide, 2,6-dichlorobenzyl (2,2-dimethyl-4-ethyldioxolan-4-yl)methyl ether, 3′,5′-dinitro-4-(di-n-propylamino)acetophenone, N-chloroacetyl-N-(2,6-diethylphenyl) glycine ethyl ester, 2,3:4,6-di-O-isopropylidene-2-keto-L-gulonate, 1-m-trifluoromethylphenyl-4-dimethylamino-5-chloropyridazone, 4-amino-3-methy-6-phenyl-1,2,4-triazin-5-(4H)-one, N-(2-methoxy-1-methylethyl)-2′-ethyl-6′-methyl-2-chloroacetanilide, O-(N-phenylcarbamoyl)-propanone oxime, N-(4-methyl-3-(trifluoromethylsulphonylamino)phenyl)acetamide, 2,2,3,3-tetrafluoropropionic acid, (1-methylethyl)-O-methyl-O-(4-methyl-2-nitrophenyl)phosphoramidothioate, N-benzyl-N-isopropyl-3,5-dimethylbenzamide, S-(4-methoxybenzyl)-N,N-diethylcarbamothioate, 2-chloro-6-(2-cyano-1-methylethylamino)-4-cyclopropylamino-s-triazine,2,2-dimethyl-N-benzyl-N-isopropylpropionamide, 3-[5-(1,1-dimethylethyl)-1,3,4-thiadia-1-2-yl]-4-hydroxy-1-methyl-2-imidazolidinone, N-(3-chloro-4-ethoxyphenyl)-N′,N′-dimethylurea, 1-methyl-4-phenylpyridinium chloride, N-[5-(2-chloro-1,1-dimethylethyl)-1,3,4-thiadiazol-2-yl]cyclopropane carboxamide, 4-t-butyl-N-s-butyl-2,6-dinitroaniline, 1,1′-di(diethylcarbamoylmethyl)-4,4′-bipyridylium dichloride, 2-t-butyl-4-(2-chloro-4-(3,3-dimethylureido)phenyl)-1,3,4-oxadiazolin-5-one, 2′,6′-dimethyl-N-(2-methoxyethyl)-2-chloroacetanilide, α-[4-(4′-chlorophenoxy)phenoxy]-propionic acid isobutyl ester, α-[4-(2′,4′-dichlorophenoxy)phenoxy]propionic acid methyl ester, N-ethyl-N-propyl-3-(propylsulphonyl)-1H-1,2,4-triazole-1-carboxamide, tris-(2-methoxyethoxy)-2′-chloroethylsilane, N-ethyl-N-(2-methyl-2-propenyl)-2,6-dinitro-4-(trifluoromethyl)aniline, N-2-chloroethyl(-2,6-dinitro-N-propyl-4-(trifluoromethyl)aniline, methyl N-benzoyl-N-(3-chloro-4-fluorophenyl)-2-aminopropionate, isopropyl N-benzoyl-N-(3-chloro-4-fluorophenyl)-2-aminopropionate, 2,4-dichloro-6-fluorophenyl 4-nitrophenyl ether, N-3-(1′,1′,2′,2′-tetrafluoroethoxy)phenyl-N′,N′-dimethylurea, 1-methyl-3-phenyl-5-[3-(trifluoromethyl)phenyl]-4-(1H)-pyridinone, 2-amino-4-isopropylamino-6-chloropyrimidine, 6-t-butyl-4-isobutylideneamino-3- methylthio-1,2,4-triazin-5-(4H)-one,α-(4-chlorophenyl)-α-(1-methylethyl)-5-pyrimidinemethanol, 2-(2,4,5-trichlorophenoxy)ethanol, N-[2,4-dimethyl-5-(((trifluoromethyl)sulphonyl)amino)phenyl]acetamide, 2-chloroethyl-tris(methoxy)silane+α,ω-bis(2-chloroethyl)-α,α,ω,ω-tetramethoxypoly[(2-chloroethyl)methoxy]siloxane, O-ethyl-O-(3-methyl-6-nitrophenyl)-N-s-butylphosphorothioamidate, N-(2'-methoxy-1'-methylethyl)-2'-ethyl-6'-methyl-2-chloro-acetanilide, N-(2-methyl-2-propenyl)-2,6-dinitro-N-propyl-4-(trifluoromethyl) aniline, 2-(4-ethylamino-6-methylthio-s-triazin-2-ylamino)-2-methylpropionitrile, N-(1-phenyl-5-bromo-6-oxopyridazin-4-yl) oxamic acid sodium salt, 1,1,1-trifluoro-N-[2-methyl-4-(phenylsulphonyl)-phenyl]methane sulphonamide, 3-ethoxycarbonylaminophenyl N-phenylcarbamate, ammonium ethyl carbamoylphosphonate, 1-allyl-1-tetrahydrogeranylpiperidinium bromide, N-((4-dipropylamino)-3,5-dinitrophenyl)sulphonyl)-S,S-dimethylsulphilimine, 2-chloro-N-(1-methyl-2-propynyl)acetanilide, N-(5-butylsulphonyl-1,3,4-thiadiazol-2-yl)-N,N'-dimethylurea, 1-[O-(methylsulphamoyl) glycoloyl]hexahydroazepine, 1,3-dimethyl-1-5-dimethylsulphamoyl-1,3,4-thiadiazol-2-yl)urea, 1-(5-ethylsulphonyl-1,3,4-thiadiazol-2-yl)-1,3-dimethylurea, 1-(5-t-butyl-1,3,4-thiadiazol-2-yl)-1,3-dimethylurea, N-(butoxymethyl)-2-chloro-N-(2-(1,1-dimethylethyl)-6-methylphenyl)acetamide, 3-(3-chloro-4-chlorodifluoromethylthiophenyl)-1,1-dimethylurea, [(3,5,6-trichloro-2-pyridinyl)oxy]acetic acid, 2-[4-(4-trifluoromethylphenoxy)phenoxy)]propionic acid methyl ester, and 3-cyclohexyl-6-(dimethylamino)-1-methyl-s-triazine-2,4-(1H,3H)-dione.

Specific preferred admixtures are those of 2-methyl-3-amino-6-t-butyl-2,5-dihydropyrazolo[3,4-d]pyrimidin-4-one or 2-methyl-3-amino-6-trifluoromethyl-2,5-dihydropyrazolo[3,4-d]pyrimidin-4-one or the 3-dimethylamino analogue of either with at least one of 2-ethoxy-2,3 dihydro-3,3-dimethylbenzofuran-5-yl methanesulphonate, 4-amino-3-methyl-6-phenyl-1,2,4-triazin-5-(4H)-one, 3-m-tolyl-carbamoyloxyphenylcarbamate, 5-amino-4-chloro-2-phenylpyridazin-3-one and 3-cyclohexyl-5,6-trimethyleneuracil.

The invention also provides a two-container pack in which one or more compounds of formula I are provided in a first container, and one or more further pesticides, plant growth regulants or fertilizers are provided in a second container, especially in relative proportions as described hereinafter. Desirably, the two-container pack bears or contains instructions, either separate or in conjunction with one of the containers, for mixing the contents of the containers or separately applying the contents thereof.

The ratio by weight of the compound(s) of the present invention to the second herbicide may vary over a wide range according to the particular compounds employed and the intended use. In general, however, the ratio by weight of the compound(s) of the present invention to the second herbicidal component will be from 99:1 to 1:99, more preferably from 1:15 to 10:1, desirably from 5:1 to 1:5, and especially from 3:1 to 1:3.

The compounds of the present invention may, if desired, be employed in admixture with non-phytotoxic oils.

The compounds of the present-invention may be applied to plants, the soil, land or aquatic areas. They are of especial use as selective herbicides in crops, e.g. cotton, sunflowers, or a food crop such as cereals, sugar beet, peas, beans, carrots, soya beans, maize, rice and potatoes. They may be applied pre- or post-planting of the crop, and may be employed post-emergence or preferably pre-emergence. When used in cereals, they are preferably applied with one or more plant-growth hormones.

The compounds of formula I are preferably applied in an amount in total of from 0.1 to 20 kg/ha, more preferably 1 to 10 kg/ha, especially 2.5 to 8 kg/ha.

The invention will now be further described, though only by way of illustration, in the following Examples.

EXAMPLE 1

2-Methyl-3-amino-6-t-butyl-2,5-dihydropyrazolo[3,4-d]pyrimidin-4-one (a) 3,5-Diamino-4-cyano-1-methylpyrazole (IV)

Sufficient concentrated hydrochloric acid was added to a solution of methylhydrazine (9.2 g) in water (30 ml) to give a pH of 1. Potassium tricyanomethanide (28 g) was added and the solution was heated under reflux for 20 hours and then cooled to precipitate 21.5 g (yield 80%) of 3,5-diamino-4-cyano-1-methylpyrazole. A sample was recrystallised from water, mp 194° C. with decomposition.

Analysis: Found: C 44.05% H 5.0% N 51.15%: $C_5H_9N_5$ requires: C 43.8% H 5.15% N 51.05%.

(b)
5-amino-4-cyano-3-(2,2-dimethylpropanoylamino)-1-methyl pyrazole (V)

Pivaloyl chloride (2,2-dimethylpropionyl chloride) (3.6 g) was added cautiously to a suspension of 3,5-diamino-4-cyano-1-methylpyrazole (4.1 g) in pyridine (25 ml). The temperature of the mixture rose to about 60°. The mixture was left to cool overnight and was then poured into a mixture of ice (60 g) and concentrated HCl (40 ml). The precipitate was filtered off, washed and dried, to give 3.9 g of crude 5-amino-4-cyano-3-(2,2-dimethylpropanoylamino)-1-methylpyrazole. Recrystallisation from a 70:30 ethanol/water mixture gave 3.1 g of pure product, mp 245°–247° C.

Analysis: Found: C 54.0% H 6.55% N 31.3%: $C_{10}H_{15}N_5O$ requires: C 54.3% H 6.85% N 31.65%.

(c)
2-Methyl-3-amino-6-t-butyl-2,5-dihydropyrazolo[3,4-d]pyrimidin-4-one (I)

5-amino-4-cyano-3-(2,2-dimethylpropionamido)-1-methylpyrazole (12.5 g) and 1 N sodium hydroxide solution (115 ml) were heated together for 2 hours to give the sodium salt of the desired product. A trace of solid was filtered off and the filtrate was cooled to 10° and adjusted to pH 7 with concentrated HCl to liberate the free desired compound. A precipitate formed after a few minutes and it was filtered off, water-washed and recrystallised whilst-still water wet, from ethanol, to give 6.1 g of 2-methyl-3-amino-6-t-butyl-2,5-dihydropyrazolo[3,4-d]pyrimidin-4-one, mp 285°–287° C.

Analysis: Found: C 54.35% H 6.95% N 32.0%: $C_{10}H_{15}N_5O$ requires: C 54.3 H 6.85% N 31.65%.

EXAMPLE 2

2-Methyl-3-amino-6-trifluoromethyl-2,5-dihydropyrazolo[3,4-d]pyrimidin-4-one (a) 3,5-diamino-1-methylpyrazole-4-carboxamide (III)

A solution of methylhydrazine (18.4 g) in water (60 ml) was adjusted to pH 3-4 by adding concentrated HCl (approximately 36 ml). The potassium salt of dicyanoacetamide (64 g) was added and the solution was heated under reflux for 44 hours and then cooled to 0° to precipitate 28.5 g of crude 3,5-diamino-1-methylpyrazole-4-carboxamide, a sample of which was recrystallised from isopropanol/water, mp 213°-215° C.

Analysis: Found: C 38.3% H 5.75% H 44.85%: $C_5H_9N_5O$ requires: C 38.7% H 5.85% N 45.15%.

(b) 2-Methyl-3-amino-6-trifluoromethyl-2,5-dihydropyrazolo[3,4-d]pyrimidin-4-one (I)

3,5-diamino-1-methyl-pyrazole-4-carboxamide (12 g) was heated with trifluoroacetic acid (18 ml) for 7½ hours. The mixture was poured into 2 N sodium hydroxide solution (150 ml) to give the sodium salt of the desired product, and the resultant solution was acidified (to pH ~4) with concentrated HCl to precipitate 11.8 g of 2-methyl-3-amino-6-trifluoromethyl-2,5-dihydropyrazolo[3,4-d]pyrimidin-4-one, mp >360° C.

Analysis: Found: C 35.85% H 2.5% N 29.7%: $C_7H_6F_3N_5O$ requires: C 36.05% H 2.6% N 30.05%.

EXAMPLES 3-7

The following compounds of formula IV were prepared by processes analogous to those described in Example 1(a), except where otherwise stated:
3. 3,5-diamino-4-cyanopyrazole, m.p. 167°-169° C.;
4. 3,5-diamino-4-cyano-1-phenylpyrazole, m.p. 206°-208° C.;
5. 3,5-diamino-4-cyano-1-(2-hydroyethyl)pyrazole, m.p. 128°-129° C.;
6. *3,5-diamino-4-cyano-1-propylpyrazole, m.p. 108°-109° C.
7. *3,5-diamino-4-cyano-1-butylpyrazole, m.p. 134°-135° C.

* - compounds prepared employing the appropriate hydrazine sulphate with half neutralization by potassium carbonate or sodium hydroxide instead of hydrazine and hydrochloric acid.

EXAMPLE 8

3,5-Diamino-4-cyano-1-methylpyrazole (IV)

3,5-Diamino-4-cyanopyrazole (6.1 g) prepared as in Example 3, iodomethane (3.1 ml), anhydrous potassium carbonate (7.6 g) and acetone (120 ml) were heated under reflux for 18 hours. The mixture was filtered, and the filtrate was concentrated to a viscous oil. Trituration of the oil with water gave a precipitate of 3,5-diamino-4-cyano-1-methylpyrazole (1.1 g), m.p. 194°-196° C.

EXAMPLES 9-10

The following compounds of formula IV were prepared by processes analogous to that described in Example 8, except that iodoethane and iodobutane were respectively employed in place of the iodomethane:
9. 3,5-diamino-4-cyano-1-ethylpyrazole;
10. 3,5-diamino-4-cyano-1-butylpyrazole.

EXAMPLE 11

3,5-Diamino-4-cyano-1-methylpyrazole (IV)

3,5-Diamino-4-cyanopyrazole (6.1 g) was dissolved in 1 M sodium hydroxide solution (50 ml), and dimethylsulphate (6.2 g) was added. The mixture was heated at reflux for 2½ hours and then evaporated to dryness. The residue was extracted with 2-methoxyethanol, and the extracts were evaporated. The residue was triturated with a small amount of water to give 3,5-diamino-4-cyano-1-methylpyrazole (1.4 g), m.p. 194°-196° C.

EXAMPLE 12

3,5-Diamino-4-cyano-1-methylpyrazole (IV)

Amino-(methylmercapto)-methylenemalononitrile (X) (0.7 g), methyl hydrazine (0.3 g) and water (4 ml) were heated under reflux for 2 hours. On cooling, 3,5-diamino-4-cyano-1-methylpyrazole (0.4 g) precipitated, m.p. 197°-198° C.

EXAMPLES 13-15

The following compounds of formula IV were prepared by processes analogous to that of Example 12, but employing hydrazine hydrate with the appropriate alkylamino-(methylmercapto)-methylenemalononitrile:
13. 3,5-diamino-4-cyanopyrazole;
14. 3-amino-4-cyano-5-methylaminopyrazole;
15. 3-amino-4-cyano-5-isobutylaminopyrazole.

EXAMPLE 16

3-Amino-4-cyano-1-methyl-5-methylaminopyrazole (IV)

(a) Benzaldehyde N-methyl-N-(2,2-dicyano-1-methylmercaptoethenyl) hydrazone (VII)

Methyl hydrazine (4.2 g) was added slowly to benzaldehyde (9.4 ml) in 2-methoxyethanol (15 ml) causing the solution to boil. The solution was heated under reflux for 20 minutes and was then added to a solution of bis(methylmercapto)methylenemalononitrile (15.6 g) in 2-methoxyethanol (75 ml). The solution was heated under reflux for 6 hours and was then cooled to 0° C. to precipitate benzaldehyde N-methyl-N-(2,2-dicyano-1-methylmercaptoethenyl) hydrazone (5.6 g), m.p. 159°-160° C.

Analysis: Found: C 60.6, H 4.65, N 21.95%: $C_{13}H_{12}N_4S$ requires: C 60.9, H 4.7, N 21.85%.

(b) Benzaldehyde N-methyl-N-[2,2-dicyano-1-(dimethylamino) ethenyl]hydrazone (VI)

The product of stage (a) (26 g), aqueous dimethylamine (6.6 g) and ethanol (250 ml) were heated under reflux for 4 hours and then cooled to 0° C. Benzaldehyde N-methyl-N-[2,2-dicyano-1-(dimethylamino)ethenyl]hydrazone (19.8 g) precipitated, m.p. 127°-128° C.

Analysis: Found: C 66.6, H 6.1, N 28.0%: $C_{14}H_{15}N_5$ requires: C 66.4, H 5.95, N 27.65%.

(c) 3-Amino-4-cyano-1-methyl-5-dimethylaminopyrazole (IV)

The product of stage (b) (19 g) was heated for 20 minutes with 1 M hydrochloric acid. The mixture was cooled and benzaldehyde was removed by extraction with dichloromethane. The aqueous phase was neutralised with sodium hydroxide to precipitate 3-amino-4-cyano-1-methyl-5-dimethylaminopyrazole (7.2 g), m.p. 100°–102° C.

Analysis: Found: C 51.1, H 7.05 N 42.8%: $C_7H_{11}N_5$ requires: C 50.9, H 6.7, N 42.4%.

EXAMPLE 17

3-Amino-4-cyano-1-methyl-5-methylaminopyrazole (IV)

By a process analogous to that described in Example 16, but employing ethanolic methylamine in stage (b) instead of ethanolic dimethylamine, the compound benzaldehyde N-methyl-N-[2,2-dicyano-1-(methylamino)ethenyl]hydrazone (VI), m.p. 218°–220° C. was prepared, which was converted into 3-amino-4-cyano-1-methyl-5-methylaminopyrazole (4.8 g).

Analysis: Found: C 48.0 H 6.25 N 46.0: $C_6H_9N_5$ requires: C 47.65, H 6.0, N 46.35.

EXAMPLES 18–29

The following compounds of formula V were prepared from compounds of formula IV prepared as in the above Examples, by processes analogous to those described in Example 1(b).

18. 5-amino-4-cyano-3-propanoylamino-1-methylpyrazole;
19. 5-amino-4-cyano-3-benzylamino-1-methylpyrazole, m.p. 203°–205° C.;
20. 5-amino-4-cyano-3-(2-methylpropanoylamino)-1-methylpyrazole, m.p. 197°–198° C.;
21. 5-amino-4-cyano-3-(2-furoylamino)-1-methylpyrazole, m.p. 211°–213° C.;
22. 5-amino-4-cyano-3-(2,2-dimethylpropanoylamino)-1-ethylpyrazole;
23. 5-amino-4-cyano-3-(2,2-dimethylpropanoylamino)-1-propylpyrazole;
24. 5-amino-4-cyano-3-(2,2-dimethylpropanoylamino)-1-butylpyrazole;
25. 5-dimethylamino-4-cyano-3-(2,2-dimethylpropanoylamino)-1-methylpyrazole, m.p. 135°–137° C.;
26. 5-methylamino-4-cyano-3-(2,2-dimethylpropanoylamino)-1-methylpyrazole, m.p. 189°–191° C.;
27. 5-amino-4-cyano-3-(3-methylbutanoylamino)-1-methylpyrazole, m.p. 210°–211° C.;
28. 5-amino-4-cyano-3-isobutyrylamino-1-propylpyrazole;
29. 5-amino-4-cyano-3-(2,2-dimethylpropanoylamino)-1-(2-hydroxyethyl)pyrazole.

EXAMPLES 30–36

The following compounds of formula V were believed to be prepared, but were not isolated, in the preparation of the compounds of Examples 37 to 43, in which, as a first stage, appropriate compounds of formula IV prepared as in the above Examples were heated under reflux with trifluoroacetic acid (about 20 parts of acid per 7.3 parts of compound of formula IV) for about 5 hours:

30. 5-amino-4-cyano-3-trifluoroacetylamino-1-methylpyrazole;
31. 5-amino-4-cyano-3-trifluoroacetylaminopyrazole;
32. 5-amino-4-cyano-3-trifluoroacetylamino-1-(2-hydroxyethyl) pyrazole;
33. 5-(2-methylpropylamino)-4-cyano-3-trifluoroacetylaminopyrazole;
34. 5-dimethylamino-4-cyano-3-trifluoroacetylaminopyrazole;
35. 5-methylamino-4-cyano-3-trifluoroacetylaminopyrazole;
36. 5-methylamino-4-cyano-3-trifluoroacetylamino-1-methylpyrazole.

EXAMPLES 37–54

The following compounds of formula I were prepared from compounds of formula V prepared as in the above Examples by processes analogous to that described in Example 1(c), no intermediates of formula II being isolated:

37. 2-methyl-3-amino-6-trifluoromethyl-2,5-dihydropyrazolo[3,4-d]pyrimidine-4-one;
38. 3-amino-6-trifluoromethyl-2,5(or 1,5)-dihydropyrazolo[3,4-d]pyrimidine-4-one, m.p. 300° C.;
39. 2-(2-hydroxyethyl)-3-amino-6-trifluoromethyl-2,5-dihydropyrazolo[3,4-d]pyrimidin-4-one, m.p. 319°–320° C. decomp;
40. 3-(2-methylpropylamino)-6-trifluoromethyl-2,5(or 1,5)-dihydropyrazolo[3,4-d]pyrimidin-4-one, m.p. 330°–332° C. decomp;
41. 2-methyl-3-dimethylamino-6-trifluoromethyl-2,5-dihydropyrazolo[3,4-d]pyrimidin-4-one; m.p. 264°–265° C.;
42. 3-methylamino-6-trifluoromethyl-2,5(or 1,5)-dihydropyrazolo[3,4-d]pyrimidin-4-one, m.p. 355° C. decomp;
43. 2-methyl-3-methylamino-6-trifluoromethyl-2,5-dihydropyrazolo[3,4-d]pyrimidin-4-one, m.p. 360°;
44. 2-methyl-3-amino-6-ethyl-2,5-dihydropyrazolo[3,4-d]pyrimidin-4-one, m.p. 322°–324° C. decomp;
45. 2-methyl-3-amino-6-phenyl-2,5-dihydropyrazolo[3,4-d]pyrimidin-4-one, m.p. 326°–330° C. decomp;
46. 2-methyl-3-amino-6-isopropyl-2,5-dihydropyrazolo[3,4-d]pyrimidin-4-one, m.p. 290°–294° C.;
47. 2-methyl-3-amino-6-(2-furyl)-2,5-dihydropyrazolo[3,4-d]pyrimidin-4-one, m.p. 307°–309° C.;
48. 2-ethyl-3-amino-6-(1,1-dimethylethyl)-2,5-dihydropyrazolo[3,4-d]pyrimidin-4-one, m.p. 292°–294° C.;
49. 2-propyl-3-amino-6-(1-methylethyl)-2,5-dihydropyrazolo[3,4-d]pyrimidin-4-one, m.p. 113°–114° C.;
50. 2-propyl-3-amino-6-(1,1-dimethylethyl)-2,5-dihydropyrazolo[3,4-d]pyrimidin-4-one, m.p. 244°–246° C.;
51. 2-butyl-3-amino-6-(1,1-dimethylethyl)-2,5-dihydropyrazolo[3,4-d]pyrimidin-4-one, m.p. 228°–229° C.;
52. 2-(2-hydroxyethyl)-3-amino-6-(1,1-dimethylethyl)-2,5-dihydropyrazolo[3,4-d]pyrimidin-4-one; m.p. 255°–256° C.;
53. 2-methyl-3-dimethylamino-6-(1,1-dimethylethyl)-2,5-dihydropyrazolo[3,4-d]pyrimidin-4-one, m.p. 287°–289° C.;
54. 2-methyl-3-methylamino-6-(1,1-dimethylethyl)-2,5-dihydropyrazolo[3,4-d]pyrimidin-4-one, m.p. 349° C. decomp.

EXAMPLE 55

3,5-Diamino-1-phenylpyrazole-4-carboxamide (III)

The above compound was prepared by a process analogous to that described in Example 2(a), m.p. 182°-183° C., but starting instead with phenylhydrazine.

Analysis: Found: C 55.6, H 5.25, N 32.3%: $C_{10}H_{11}N_5O$ requires: C 55.3, H 5.1, N 32.25%.

EXAMPLE 56

3-Amino-2-phenyl-6-trifluoromethyl-2,5-dihydropyrazolo[3,4-d]pyrimidin-4-one (I)

The above compound was prepared from 3,5-diamino-1-phenylpyrazole-4-carboxamide prepared as in example 55 by a process analogous to that described in Example 2(b). Melting point 267°-269° C.

Analysis: Found: C 48.8, H 2.8, N 23.45%: $C_{12}H_8F_3N_5O$ requires: C 48.8, H 2.75, N 23.7%.

EXAMPLE 57

3-Amino-2-phenyl-6-methyl-2,5-dihydropyrazolo[3,4-d]pyrimidin-4-one (I)

3,5-Diamino-1-phenylpyrazole-4-carboxamide (10.8 g) prepared as in Example 58 was heated with acetic acid (15 ml) and acetic anhydride (5.1 g) for 16 hours. The solution was poured into 2 M sodium hydroxide solution (200 ml) and a trace of solid was filtered off. The filtrate was adjusted to pH=7 with concentrated hydrochloric acid to precipitate 3-amino-2-phenyl-6-methyl-2,5-dihydropyrazolo[3,4-d]pyrimidin-4-one (6.1 g) which was recrystallised from 2-methoxyethanol (3.6 g yield), m.p. 279°-281° C.

Analysis: Found: C 60.1, H 4.65, N 29.35%: $C_{12}H_{11}N_5O$ requires: C 59.75, H 4.6, N 29.05%.

EXAMPLE 58

3-Amino-2-phenyl-6-(1,1-dimethylethyl)-2,5-dihydropyrazolo[3,4-d]pyrimidin-4-one (I)

The above compound, m.p. 214°-216° C. was prepared by a process analogous to that described in Example 57.

EXAMPLE 59

5-Amino-4-cyano-1-(2,2-dimethylpropanoyl)-3-(2,2-dimethylpropanoylamino)pyrazole (v)

The above compound was prepared from 3,5-diamino-4-cyanopyrazole, prepared as in Example 13, by reaction thereof with two moles of pivaloyl chloride in pyridine in an analogous manner to that described in Example 1(b). Melting point 181°-184° C.

Analysis: Found: C 58.0, H 7.25, N 24.45%: $C_{14}H_{21}N_5O_2$ requires: C 57.7, H 7.25, N 24.05%.

EXAMPLE 60

3-amino-6-(1,1-dimethylethyl)-2,5(or 1,5)-dihydropyrazolo[3,4-d]pyrimidin-4-one (I)

The product of Example 59 (10 g) was heated, under reflux with 1 M sodium hydroxide solution (100 ml) for 3½ hours. A trace of solid was filtered off, and the filtrate was adjusted to pH 7-8 with concentrated hydrochloric acid. The mixture was cooled to 0° C. and the precipitate which formed was recrystallised from 2-methoxyethanol:water (80:20) to give the title compound (1.8 g), m.p. 331°-332° C. decomp.

Analysis: Found: C 51.95, H 6.6, N 33.65%: $C_9H_{13}N_5O$ requires: C 52.15, N 6.3, N 33.8%.

EXAMPLE 61

2-Methyl-3-acetylamino-6-t-butyl-2,5-dihydropyrazolo[3,4-d]-pyrimidin-4-one (I)

Acetyl chloride (3.8 g) was added slowly to a suspension of 2-methyl-3-amino-6-t-butyl-2,5-dihydropyrazolo[3,4-d]-pyrimidin-4-one (10.5 g) in pyridine (50 ml). The solution was left to cool overnight and then concentrated to an oil which was dissolved in 0.5 N hydrochloric acid (20 ml). Scratching induced crystallisation. The precipitate was recrystallised from 80:20 ethanol:water (1.5 g, 12%) m.p. 340°-42° decomposition.

Analysis: Found: C, 55.0; H, 6.4; N, 26.7: $C_{12}H_{17}N_5O_2$ requires: C, 54.75; H, 6.55; N, 26.6.

EXAMPLE 62

2-Methyl-3-bis(methanesulphonyl)amino-6-(1,1-dimethylethyl)-2,5-dihydropyrazolo[3,4-d]pyrimidin-4-one (I)

Methanesulphonyl chloride (12.9 g) was added slowly to a stirred mixture of 3-amino-2-methyl-6-(1,1-dimethylethyl)-2,5-dihydropyrazolo[3,4-d]pyrimidin-4-one (11 g) prepared as in Example 1, tetrahydrofuran (85 ml) and triethylamine (21 ml), causing the mixture to boil. The mixture was heated under reflux for 3 hours, and was then cooled and filtered. The filtrate was then evaporated to dryness, and the residue was washed with 80:20 ethanol/water to give the title compound, m.p. 258°-259° C.

Analysis: Found: C 38.55, H 4.85, N 18.6%: $C_{12}H_{19}N_5O_5S_2$ requires: C 38.2, H 5.05, N 18.55%.

EXAMPLE 63

2-[3-amino-6-(1,1-dimethylethyl)-2,5-dihydropyrazolo[3,4-d]pyrimidin-4-on-2-yl]ethanesulphonic acid (I)

3-Amino-2-(2-hydroxyethyl)-6-(1,1-dimethylethyl)-2,5-dihydropyrazolo[3,4-d]pyrimidin-4-one (5 g) prepared as in Example 52 was added to concentrated sulphuric acid (10 ml). The solution was kept at 130°-135° C. for 3 hours, then cooled and poured onto ice (30 g). The precipitate which formed was filtered off, water washed and dissolved in 2 M sodium hydroxide solution. A trace of solid was filtered off, and the filtrate was acidified with concentrated hydrochloric acid to re-precipitate the title compound (4.4 g), m.p. 307°-309° C. decomp.

Analysis: Found: C 39.85, H 5.55, N 20.85%: $C_{11}H_{17}N_5SO_5$ requires: C 39.85, H 5.15, N 21.15%.

EXAMPLE 64

3-Benzylideneamino-2-methyl-6-(1,1-dimethylethyl)-2,5-dihydropyrazolo[3,4-d]pyrimidin-4-one (I)

3-Amino-2-methyl-6-(1,1-dimethylethyl)-2,5-dihydropyrazolo[3,4-d]pyrimidin-4-one (2.2 g) prepared as in Example 1 was heated under reflux in benzaldehyde (6.6 ml) for 1½ hours. The solution was cooled to precipitate the product (2.4 g), m.p. 250°-253° C.

Analysis: Found: C 66.35, H 6.3, N 22.8%: $C_{17}H_{19}N_5O$ requires: C 66.0, H 6.2, N 22.65%.

EXAMPLE 65

3-Amino-2-methyl-6-(2-methylpropyl)-2,5-dihydropyrazolo[3,4-d]pyrimidin-4-one hydrochloride (I)

5-Amino-4-cyano-1-methyl-3-(3-methylbutanoylamino)pyrazole (10 g), prepared as in Example 27 was heated with 1 M sodium hydroxide solution (90 ml) for 2 hours. The solution was adjusted to pH=7 with concentrated hydrochloric acid, and was evaporated to dryness. The residue was extracted with acetone containing 5% water (100 ml). The extracts were evaporated, and the residue was dissolved in a minimum of hot ethanol. Then the solution was cooled and a precipitate which formed was filtered off. The filtrate was mixed with concentrate hydrochloric acid (5 ml) and the precipitate was recrystallised from water to give the title compound, m.p. 292°–294° C. decomp.

Analysis: Found: C 46.75, H 6.6, N 27.3%: $C_{10}H_{16}ClN_5O$ requires: C 46.6, H 6.25, N 27.2%.

EXAMPLE 66

2-Methyl-3-amino-6-t-butyl-2,5-dihydropyrazolo[3,4-d]pyrimidin-4-one hydrochloride (I)

2-Methyl-3-amino-6-t-butyl-2,5-dihydropyrazolo[3,4-d]pyrimidin-4-one (1.1 g), prepared as in Example 1, was dissolved in 15 ml of boiling 5 N hydrochloric acid. The solution was cooled to 0° C. to precipitate 0.9 g of the title hydrochloride, m.p. 286°–288° C. decomp.

EXAMPLE 67

A 50% wettable powder formulation was prepared by mixing and fluid energy milling the following:

| | |
|---|---|
| 3-amino-4-methyl-6-(trifluoromethyl)-2,5-dihydropyrazolo[3,4-d]pyrimidin-4-one | 50% |
| 'Reax 45L' (combined wetting and dispersing agent based on sodium lignin sulphonate) | 5% |
| China clay | 45% |

EXAMPLE 68

A 50% wettable powder formulation was prepared by mixing and fluid energy milling the following:

| | |
|---|---|
| 3-amino-6-tert-butyl-2-methyl-2,5-dihydropyrazolo[3,4-d]pyrimidin-4-one | 50% |
| 'Reax 45L' (combined wetting and dispersing agent based on sodium lignin sulphonate) | 5% |
| China clay | 45% |

EXAMPLE 69

Granules impregnated with 10% of herbicide were prepared from the following:

| | |
|---|---|
| 3-amino-6-tert-butyl-2-methyl-2,5-dihydropyrazolo[3,4-d]pyrimidin-4-one | 10% |
| 'Celaton MP78' (calcined diatomite granules 20/60 mesh) | 90% |

A 12.5% solution of the compound in a mixture of 90% of butanol and 10% of water was added in three stages to the granules. The granules were then force draught dried to evaporate the solvent.

EXAMPLE 70

Granules impregnated with 10% of herbicide were prepared from the following:

| | |
|---|---|
| 3-amino-6-tert-butyl-2-methyl-2,5-dihydropyrazolo[3,4-d]pyrimidin-4-one | 10% |
| 'Attapulgus 25/50 mesh A RVM (attapulgite granules) | 90% |

A 12.5% solution of the compound in a mixture of 90% of butanol and 10% of water was added in four stages to the granules, with forced draught drying to evaporate the solvent after the second and fourth stages.

EXAMPLE A

Seeds of peas, mustard, linseed, ryegrass, sugarbeet, oats and french beans were sown in anodised aluminium pans, 19 cm long×9.5 cm wide×5 cm deep containing John Innes I potting compost. They were then watered and placed in a controlled environment room (22° C.; 65–85% R.H.; 14 hours artificial illumination at 1200 foot canldes). Fourteen days after sowing, the seedlings received a foliar spray of each of the compounds of Examples 2, 41, 43, 53 and 54 formulated as an aqueous suspension together with 1000 ppm of the wetting agent Lissapol NX (nonyl phenol condensed with ethylene oxide). The concentrations of active ingredient and volume of application were adjusted so as to be equivalent to rates of 11.2, 2.8 and 0.7 kg/ha in 450 liters per hectare. After seven days growth in in a controlled environment room the plants were visually assessed for any herbicidal or growth regulant response. All differences from the untreated control were scored according to a herbicidal index where 0=no effect and 100=complete kill. The results are summarised in the following table:

| Compound of Example No. | 2 | 41 | | 43 | 53 | | 54 |
|---|---|---|---|---|---|---|---|
| Dosage rate (kg/ha) | 11.2 | 2.8 | 2.8 | 0.7 | 2.8 | 2.8 | 0.7 | 2.8 |
| Peas (*Pisum sativum*) | 40 | 15 | 75 | 30 | 5 | 35 | 5 | 0 |
| Mustard (*Sinapis alba*) | 100 | 100 | 100 | 100 | 85 | 100 | 100 | 85 | 0 |
| Linseed (*Linum usitatissimum*) | 100 | 100 | 100 | 25 | 0 | 100 | 40 | 30 |
| Ryegrass (*Lolium perenne*) | 100 | 65 | 100 | 80 | 15 | 95 | 85 | 5 |
| Sugarbeet (*Beta vulgaris*) | 10 | 15 | 100 | 95 | 45 | 100 | 95 | 20 |
| Oat (*Avena sativa*) | 100 | 90 | 100 | 85 | 0 | 95 | 85 | 0 |
| French beans (*Phaseolus vulgaris*) | 100 | 50 | 95 | 15 | 0 | 95 | 5 | 0 |

EXAMPLE B

The compound of Examples 2, 41, 43, 53 and 54 formulated as an attaclay/sand dust were incorporated in John Innes I potting compost at a rate equivalent to 130 and 26 ppm weight/volume of active ingredient to soil and placed in anodised aluminium pans, 19 cm long×9.5 cm wide×5 cm deep. These rates are approximately equivalent to a soil surface application of 56 and 11.2 kg active ingredient/hectare cultivated to a depth of 5 cm. Seeds of peas, mustard, linseed, maize, oats and ryegrass were sown in the treated soil, watered and placed in a controlled environment room (22° C.; 65-85% R.H.; 14 hours artifical illumination at 1200 foot candles) for 21 days. The plants were then visually assessed for any growth regulatory or herbicidal effects. All differences from an untreated control were scored on a scale from 0-100, where 0 signifies no effect and 100 signifies complete suppression. The results are summarised in the following table:

| Compound of Example No. | 2 | 41 | 43 | 153 | 54 |
|---|---|---|---|---|---|
| Dosage rate (ppm) | 130 | 26 | 26 | 26 | 26 | 26 |
| Peas (*Pisum sativum*) | 100 | 95 | 90 | 85 | 85 | 30 |
| Mustard (*Sinapis alba*) | 100 | 100 | 100 | 100 | 100 | 100 |
| Linseed (*Linum usitatissimum*) | 100 | 100 | 100 | 100 | 100 | 100 |
| Maize (*Zea mays*) | 100 | 90 | 85 | 100 | 85 | 30 |
| Oats (*Avena sativa*) | 100 | 100 | 100 | 100 | 100 | 95 |
| Ryegrass (*Lolium perenne*) | 100 | 100 | 100 | 100 | 100 | 95 |

EXAMPLE C

Seeds of various dicotyledon species, listed in the table below, were sown in anodised aluminium pans, 19 cm long × 9.5 cm wide × 5 cm deep and placed in a controlled environment room (22° C.: 65-85% R.H.; 14 hours artificial illumination at 1600 foot candles). When all species had cotyledons plus at least two fully expanded true leaves they received a foliar spray of each of the compounds of 2, 41 and 53 formulated as an aqueous suspension together with 1000 ppm of the wetting agent Lissapol NX. One pan of each species received the equivalent of 2.8 kg in 450 liters/hectare and were returned to the controlled environment room. Fourteen days after treatment the plants were visually assessed for any growth regulatory or herbicidal effect. All differences from an untreated control were scored on a scale from 0-100 where 0 signifies no effect and 100 signifies complete suppression. The

| Compound of Example No. | 2 | 41 | | 53 |
|---|---|---|---|---|
| Dosage rate kg/ha | 2.8 | 0.7 | 1.4 | 1.4 |
| Chickweed (*Stellaria media*) | 90 | 95 | 100 | 85 |
| Mayweed (*Mactreicaria spp*) | 50 | 100 | 100 | 100 |
| Cleavers (*Galium aparine*) | 55 | 95 | 100 | 100 |
| Fathen (*Chenopodium album*) | 70 | 100 | 100 | 100 |
| Corn marigold (*Chrysanthemum segetum*) | 80 | 100 | 100 | 100 |
| Pale persicaria (*Polygonum lapathifolium*) | 75 | 85 | 100 | 100 |

-continued

| Compound of Example No. | 2 | 41 | | 53 |
|---|---|---|---|---|
| Dosage rate kg/ha | 2.8 | 0.7 | 1.4 | 1.4 |
| Pigweed (*Amaranthus retroflexus*) | 55 | 100 | 100 | 100 |

EXAMPLE D

The compounds of Examples 2,41,43,53 and 54 are formulated as (I) an attaclay/sand dust and incorporated in John Innes I potting compost at a rate equivalent to 6.5 ppm weight/volume of active ingredient to soil and placed in anodised aluminium pans, 19 cm long × 9.5 cm wide × 5 cm high. This is approximately equivalent to a surface application of 2.8 kg active ingredient per hectare cultivated to a depth of 5 cm. Seeds of the species listed below were sown in the treated soil, one species per pan, watered and placed in a controlled environment room (22° C.; 65-86% R.H. and 14 hours artificial illumination at 1600 foot candles) for 21 days; (II) An aqueous suspension together with 1000 ppm of the wetting agent Lissapol NX. The surfaces of an additional set of pans with seeds already sown were then sprayed with 2.8 l kg/ha in 450 liters/hectare. The plants were then visually assessed for any growth regulatory or herbicidal effects. All differences from an untreated control were scored on a scale from 0-100, where 0 signifies no effect and 100 signifies complete suppression. The results are summarised in the following table:

| Compound of Example No. | 2 | 41 | 43 | 53 | 54 | 2 | 41 | 43 | 53 | 54 |
|---|---|---|---|---|---|---|---|---|---|---|
| Application rate (ppm) | Soil incorporation (6.5) | | | | | Surface spray (6.5) | | | | |
| Chickweed (*Stellaria media*) | 95 | 100 | 100 | 100 | 95 | 100 | 100 | 25 | — | 25 |
| Mustard (*Sinapis alba*) | 100 | 100 | 100 | 100 | 100 | 100 | 100 | 85 | — | 100 |
| Cotton (*Gossypium sp*) | 10 | 100 | 0 | 100 | 65 | 0 | 100 | 0 | — | 0 |
| Tomato (*Lycopersicon esculentum*) | 80 | 100 | 40 | 100 | 95 | 75 | 100 | 50 | — | 75 |
| Fathen (*Chenopodium album*) | 90 | 100 | 100 | 100 | 100 | 95 | 40 | 25 | — | 85 |
| Carrot (*Daucus carota*) | 80 | 100 | 75 | 100 | 80 | 70 | 100 | 50 | 100 | 40 |
| Sugarbeet (*Beta vulgaris*) | 60 | — | — | — | — | 10 | — | — | — | — |
| Wheat (*Triticum aestivum*) | 100 | 100 | 100 | 100 | 100 | 100 | 100 | 50 | 100 | 65 |
| Barley (*Hordeum vulgare*) | 95 | 100 | 100 | 100 | 30 | 100 | 100 | 20 | 100 | 40 |
| Wild Oat (*Avena fatua*) | 100 | 100 | 100 | 100 | 100 | 95 | 100 | 85 | 100 | 100 |
| Blackgrass (Alopecurus myosuroides) | 100 | 100 | 100 | 100 | 100 | 90 | 100 | 40 | 100 | 75 |
| Barnyardgrass (*Echinochloa crus-galli*) | 50 | 100 | 85 | 100 | 65 | 30 | 100 | 15 | 100 | 25 |
| Crabgrass (*Digitaria sunguinalis*) | 75 | 100 | 85 | 100 | 65 | 85 | 100 | 50 | 100 | 75 |
| Mayweed (*Matricaria spp*) | 90 | — | — | — | — | 100 | — | — | — | — |

EXAMPLE E

Seeds of peas, mustard, linseed, ryegrass, sugarbeet, oats and french beans were sown in anodised aluminium pans, 19 cm long × 9.5 cm wide × 5 cm deep containing John Innes I potting compost. They were then watered and placed in a controlled environment room (22° C.; 65-85% R.H.; 14 hours artificial illumination at 1200 foot candles). Fourteen days after sowing, the seedlings received a foliar spray of the compound of Example 1 formulated as an aqueous suspension together with 1000 ppm of the wetting agent Lissapol NX. The concentrations of active ingredient and volume of application were adjusted so as to be equivalent to rate of 2.8 kg/ha in 450 liters per hectare. After seven days growth in a controlled environment room the plants were visually assessed for any herbicidal or growth regulant response. All differences from the untreated control were scored according to a herbicidal index where 0 = no effect and 100 = complete kill. The results are summarised in the following table:

| Species | Dosage rate kg/ha 2.8 |
|---|---|
| Peas (*Pisum sativum*) | 30 |
| Mustard (*Sinapis alba*) | 100 |
| Linseed (*Linum usitatissimum*) | 100 |
| Ryegrass (*Lolium perenne*) | 45 |
| Sugarbeet (*Beta vulgaris*) | 10 |
| Oat (*Avena sativa*) | 50 |
| French beans (*Phaseolus vulgaris*) | 100 |

EXAMPLE F

The compound of Example 1 formulated as an attaclay/sand dust was incorporated in John Innes I potting compost at a rate equivalent to 26 ppm weight/volume of active ingredient to soil and placed in anodised aluminium pans, 19 cm long×9.5 cm wide×5 cm deep. These rates are approximately equivalent to a soil surface application of 11.2 kg active ingredient/hectare cultivated to a depth of 5 cm. Seeds of peas, mustard, linseed, maize, oats and ryegrass were sown in the treated soil, watered and placed in a controlled environment room (22° C.; 65–85% R.H.; 14 hours artificial illumination at 1200 foot candles) for 21 days. The plants were then visually assessed for any growth regulatory or herbicidal effects. All differences from an untreated control were scored on a scale from 0–100, where 0 signifies no effect and 100 signifies complete suppression. The results are summarised in the following table:

| Species | Dosage rate (ppm) 26 |
|---|---|
| Peas (*Pisum sativum*) | 40 |
| Mustard (*Sinapis alba*) | 100 |
| Linseed (*Linum usitatissimum*) | 100 |
| Maize (*Zea mays*) | 50 |
| Oats (*Avena sativa*) | 100 |
| Ryegrass (*Lolium perenne*) | 100 |

EXAMPLE G

Seeds of various dicotyledon species, listed in the table below were sown in anodised aluminium pans, 19 cm long×9.5 cm wide×5 cm deep and placed in a controlled environment room (22° C.; 65–85% R.H.; 14 hours artificial illumination at 1600 foot candles). When all species had cotyledons plus at least two fully expanded true leaves they received a foliar spray of the compound of Example 1 formulated as an aqueous suspension together with 1000 ppm of the wetting agent Lissapol NX. One pan of each species received the equivalent of 2.8 kg in 450 liters/hectare and was returned to the controlled environment room. Fourteen days after treatment the plants were visually assessed for any growth regulatory or herbicidal effect. All differences from an untreated control were scored on a scale from 0–100 where 0 signifies no effect and 100 signifies complete suppression. The results are summarised in the following table:

| Species | Dosage rate kg/ha 2.8 |
|---|---|
| Chickweed (*Stellaria media*) | 90 |
| Mayweed (*Matricaria spp*) | 60 |
| Cleavers (*Galium aparine*) | 80 |
| Fathen (*Chenopodium album*) | 100 |
| Corn marigold (*Chrysanthemum segetum*) | 80 |
| Pale persicaria (*Polygonum lapathifolium*) | 90 |
| Pigweed (*Amaranthus retroflexus*) | 100 |

EXAMPLE H

The compound of Example 1 was formulated as an attaclay/sand dust and incorporated in John Innes I potting compost at a rate equivalent to 6.5 ppm weight/volume of active ingredient to soil and placed in anodised aluminium pans, 19 cm long×9.5 cm wide×5 cm high. This is approximately equivalent to a surface application 2.8 kg active ingredient per hectare cultivated to a depth of 5 cm. Seeds of the species listed below were sown in the treated soil, one species per pan, watered and placed in a controlled environment room (22° C.; 65–85% R.H. and 14 hours artificial illumination at 1600 foot candles) for 21 days. The plants were then visually assessed for any growth regulatory or herbicidal effects. All differences from an untreated control were scored on a scale from 0–100, where 0 signifies no effect and 100 signifies complete suppression. The results are summarised in the following table:

| Species | Dosage rate (ppm) Soil Incorporation 6.5 |
|---|---|
| Chickweed (*Stellaria media*) | 50 |
| Mustard (*Sinapis alba*) | 100 |
| Cotton (*Gossypium sp*) | 0 |
| Tomato (*Lycopersicon esculentum*) | 75 |
| Fathen (*Chenopodium album*) | 75 |
| Carrot (*Daucus carota*) | 65 |
| Sugarbeet (*Beta vulgaris*) | 10 |
| Wheat (*Triticum aestivum*) | 85 |
| Barley (*Hordeum vulgare*) | 10 |
| Wild oat (*Avena fatua*) | 100 |
| Blackgrass (*Alopecurus myosuroides*) | 85 |
| Barnyardgrass (*Echinochloa crus-galli*) | 0 |
| Crabgrass (*Digitaria sanguinalis*) | 10 |
| Mayweed (*Matricaria spp*) | 90 |

EXAMPLE I

Seeds of peas, mustard, linseed, ryegrass, sugarbeet, oats and french beans were sown in anodised aluminium pans, 19 cm long×9.5 cm wide×5 cm deep containing John Innes I potting compost. They were then watered and placed in a controlled environment room (22° C.; 65–85% R.H.; 14 hours artificial illumination at 1200 foot candles). Fourteen days after sowing the seedlings received a foliar spray of the compound of Example 44 formulated as an aqueous suspension together with 1000 ppm of the wetting agent Lissapol NX. The concentrations of active ingredient and volume of application were adjusted so as to be equivalent to a rate of 2.8 kg/ha in 450 liters per hectare. After seven days growth in a controlled environment room the plants were visually assessed for any herbicidal or growth regulant response. All differences from the untreated control were scored according to a herbicidal index where 0=no effect and 100=complete kill. The results are summarised in the following table:

| Species | Dosage rate kg/ha 2.8 |
|---|---|
| Peas (Pisum sativum) | 5 |
| Mustard (Sinapis alba) | 85 |
| Linseed (Linum usitatissimum) | 5 |
| Ryegrass (Lolium perenne) | 0 |
| Sugarbeet (Beta vulgaris) | 0 |
| Oat (Avena sativa) | 20 |
| French beans (Phaseolus vulgaris) | 0 |

EXAMPLE J

Seeds of peas, mustard, linseed, ryegrass, sugarbeet, oats and french beans were sown in anodised aluminium pans, 19 cm long×9.5 cm wide×5 cm deep containing John Innes I potting compost. They were then watered and placed in a controlled environment room (22° C.; 65–85% R.H.; 14 hours artificial illumination at 1200 foot candles). Fourteen days after sowing, the seedlings received a foliar spray of the compound of Example 46 formulated as an aqueous suspension together with 1000 ppm of the wetting agent Lissapol NX. The concentrations of active ingredient and volume of application were adjusted so as to be equivalent to a rate of 2.8 kg/ha in 450 liters per hectare. After seven days growth in a controlled environment room the plants were visually assessed for any herbicidal or growth regulant response. All differences from the untreated control were scored according to a herbicidal index where 0=no effect and 100=complete kill. The results are summarised in the following table:

| Species | Dosage rate kg/ha 2.8 |
|---|---|
| Peas (Pisum sativum) | 10 |
| Mustard (Sinapis alba) | 100 |
| Linseed (Linum usitatissimum) | 20 |
| Ryegrass (Lolium perenne) | 10 |
| Sugarbeet (Beta vulgaris) | 0 |
| Oat (Avena sativa) | 0 |
| French beans (Phaseolus vulgaris) | 0 |

EXAMPLE K

The compound of Example 46 formulated as an attaclay/sand dust was incorporated in John Innes I potting compost at a rate equivalent to 26 ppm weight/volume of active ingredient to soil and place in anodised aluminium pans, 19 cm long×9.5 cm wide×5 cm deep. This rate is approximately equivalent to a soil surface application of 11.2 kg active ingredient/hectare cultivated to a depth of 5 cm. Seeds of peas, mustard, linseed, maize, oats and ryegrass were sown in the treated soil, watered and placed in a controlled environment room (22° C.; 65–85% R.H.; 14 hours artificial illumination at 1200 foot candles) for 21 days. The plants were then visually assessed for any growth regulatory or herbicidal effects. All differences from an untreated control were scored on a scale from 0–100, where 0 signifies no effect and 100 signifies complete suppression. The results are summarised in the following table:

| Species | Dosage rate (ppm) 26 |
|---|---|
| Peas (Pisum sativum) | 20 |
| Mustard (Sinapis alba) | 100 |
| Linseed (Linum usitatissimum) | 55 |

-continued

| Species | Dosage rate (ppm) 26 |
|---|---|
| Maize (Zea mays) | 0 |
| Oats (Avena sativa) | 65 |
| Ryegrass (Lolium Perenne) | 55 |

EXAMPLE L

In a pre-emergence trail, applied by spraying at a rate of 11.2 kg/ha to various species, the following results were obtained where 0=no effect and 9=total kill.

| Compound of Example No. | 1 | 2 | 48 | 51 | 61 |
|---|---|---|---|---|---|
| Pea | 4 | 9 | 4 | 1 | 4 |
| Mustard | 9 | 9 | 9 | 8 | 9 |
| Linseed | 9 | 9 | 6 | 1 | 7 |
| Rye | 9 | 9 | 4 | 0 | 4 |
| Oats | 9 | 9 | 4 | 2 | 5 |
| Maize | 5 | 8 | 0 | 2 | 3 |

EXAMPLE M

In field trails, the following treatments were applied to crops of sugar beet both pre- and post-emergence:

Treatment A: ethofumesate+the compound of Example 1 to give a rate of application of 0.5 kg/ha of ethofumesate and 1.5 kg/ha of the compound of Example 1, Treatment B: ethofumesate+the compound of Example 1 to give a rate of application of 1.0 kg/ha of ethofumesate and 2.0 kg/ha of the compound of Example 1, Treatment C: ethofumesate+the compound of Example 2 to give a rate of application of 0.5 kg/ha of ethofumesate and 1.5 kg/ha of the compound of Example 2, and Treatment D: ethofumesate+the compound of Example 2 to give a rate of application of 1.0 kg/ha of ethofumesate and 2.0 kg/ha of the compound of Example 2.

Results obtained were as follows, 0 indicating no kill and 100 indicating complete kill.

| Pre-emergence | Treatment A | Treatment B | Treatment C | Treatment D |
|---|---|---|---|---|
| Sugarbeet | 5 | 15 | 10 | 15 |
| Buckwheat | 65 | 90 | 15 | 50 |
| Mustard | 85 | 85 | 80 | 70 |
| Barnyardgrass | 55 | 10 | 60 | 25 |
| Pigweed | 90 | 95 | 90 | 100 |
| Wild Oats | 55 | 75 | 75 | 75 |
| Blackgrass | 70 | 75 | 70 | 65 |

| Post-emergence | Treatment A | Treatment B | Treatment C | Treatment D |
|---|---|---|---|---|
| Buckwheat | 45 | 75 | 60 | 60 |
| Mustard | 55 | 65 | 85 | 80 |
| Pigweed | 60 | 75 | 40 | 65 |
| Sugar beet | 5 | 5 | 0 | 15 |

EXAMPLE N

Using the method of Example A but against different species as set out below, the following results were obtained:

| Compd. of Ex. No. | 41 | | | 53 | |
|---|---|---|---|---|---|
| Rate (kg/ha) | 2.8 | 1.4 | 0.7 | 2.8 | 1.4 |
| Wheat | 100 | 100 | 100 | 100 | 95 |
| Barley | 100 | 100 | 95 | 95 | 95 |
| Wild Oat | 100 | 100 | 100 | 100 | 100 |
| Blackgrass | 100 | 100 | 95 | 100 | 100 |
| Barnyardgrass | 95 | 100 | 75 | 100 | 100 |
| Crabgrass | 100 | 90 | 70 | 95 | 85 |

We claim:

1. A substituted pyrazolopyrimidine selected from the group consisting of (1) a compound of the formula

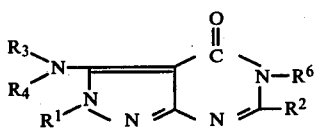

wherein $R^1$ represents hydrogen, $C_1$ to $C_6$ alkyl, $C_3$ to $C_7$ cycloalkyl or phenyl, $R^2$ represents hydrogen, $C_1$ to $C_6$ alkyl, $C_1$ to $C_6$ haloalkyl or phenyl, $R^3$ and $R^4$ are the same or different and represent hydrogen, $C_1$ to $C_6$ alkyl, $C_1$ to $C_6$ alkanoyl, or together represent benzylidene, and $R^6$ represents hydrogen or $C_1$ to $C_6$ alkyl, (2) a salt of a compound of (1) with a base and (3) an acid addition salt of a compound of (1).

2. A substituted pyrazolopyrimidine according to claim 1 wherein
   $R^1$ represents hydrogen or $C_1$ to $C_6$ alkyl,
   $R^2$ represents $C_1$ to $C_6$ alkyl, $C_1$ to $C_6$ haloalkyl or phenyl,
   $R^3$ and $R^4$ represent hydrogen, $C_1$ to $C_4$ alkyl or acetyl, and
   $R^6$ represents hydrogen.

3. A substituted pyrazolopyrimidine according to claim 2 wherein
   $R^1$ represents $C_1$ to $C_4$ alkyl,
   $R^2$ represents $C_1$ to $C_4$ alkyl, trifluoromethyl, or phenyl,
   $R^3$ represents hydrogen, methyl or acetyl,
   $R^4$ represents hydrogen or methyl, and
   $R^6$ represents hydrogen.

4. A substituted pyrazolopyrimidine according to claim 1 wherein
   $R^1$ represents methyl, ethyl, n-propyl, or n-butyl,
   $R^2$ represents methyl, ethyl, isopropyl, 5-butyl, trifluoromethyl or phenyl,
   $R^3$ represents hydrogen, methyl or acetyl,
   $R^4$ represents hydrogen or methyl, and
   $R^6$ represents hydrogen.

5. A substituted pyrazolopyrimidine according to claim 1 said compound being 2-methyl-3-amino-6-t-butyl-2,5-dihydropyrazolo[3,4-d]pyrimidin-4-one, 2-methyl-3-methylamino-6-t-butyl-2,5-dihydropyrazolo[3,4-d]pyrimidin-4-one, 2-methyl-3-dimethylamino-6-t-butyl-2,5-dihydropyrazolo[3,4-d]pyrimidin-4-one, 2-methyl-3-amino-6-ethyl-2,5-dihydropyrazolo[3,4-d]pyrimidin-4-one, 2-methyl-3-amino-6-phenyl-2,5-dihydropyrazolo[3,4-d]pyrimidin-4-one, 2-methyl-3-amino-6-isopropyl-2,5-dihydropyrazolo[3,4-d]pyrimidin-4-one, 2-methyl-3-amino-6-trifuloromethyl-2,5-dihydropyrazolo[3,4-d]pyrimidin-4-one, 2-methyl-3-dimethylamino-6-trifluoromethyl-2,5-dihydropyrazolo[3,4-d]pyrimidin-4-one, 2-ethyl-3-amino-6-t-butyl-2,5-dihydropyrazolo[3,4-d]pyrimidin-4-one, 2-methyl-3-acetylamino-6-t-butyl-2,5-dihydropyrazolo[3,4-d]pyrimidin-4-one, or 2-n-butyl-3-amino-6-t-butyl-2,5-dihydropyrazolo[3,4-d]pyrimidin-4-one.

6. A substituted pyrazolopyrimidine according to claim 1 wherein $R^1$ represents $C_1$ to $C_4$ alkyl.

7. A substituted pyrazolopyrimidine according to claim 1 wherein $R^3$ and $R^4$ both represent hydrogen, both represent $C_1$ to $C_6$ alkyl, or one represents hydrogen and the other represents $C_1$ to $C_6$ alkyl.

8. A substituted pyrazolopyrimidine according to claim 1 wherein $R^6$ represents hydrogen.

9. A substituted pyrazolopyrimidine according to claim 1 wherein
   $R^1$ is methyl,
   $R^2$ is t-butyl,
   $R^3$ and $R^4$ are both hydrogen, both methyl, or one is hydrogen and the other is methyl, and
   $R^6$ is hydrogen.

10. A substituted pyrazolopyrimidine according to claim 1 wherein
    $R^1$ is methyl,
    $R^2$ is trifluoromethyl,
    $R^3$ and $R^4$ are both hydrogen, both methyl or one is hydrogen and the other is methyl, and
    $R^6$ is hydrogen.